(12) United States Patent
Balu-Iyer et al.

(10) Patent No.: US 11,083,782 B2
(45) Date of Patent: Aug. 10, 2021

(54) PHOSPHOSERINE CONTAINING COMPOSITIONS FOR IMMUNE TOLERANCE INDUCTION

(71) Applicant: The Research Foundation for The State University of New York, Amherst, NY (US)

(72) Inventors: Sathy Balu-Iyer, Amherst, NY (US); Richard Bankert, Eden, NY (US); Radha Ramakrishnan, Plainsboro, NJ (US); Robert Dingman, Henrietta, NY (US); Vandana Iyer, Amherst, NY (US); Jennifer Schneider, Boston, MA (US); Fiona Yau Glassman, Central Islip, NY (US); Nhan Hanh Nguyen, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 137 days.

(21) Appl. No.: 16/091,425

(22) PCT Filed: Apr. 5, 2017

(86) PCT No.: PCT/US2017/026200
§ 371 (c)(1),
(2) Date: Oct. 4, 2018

(87) PCT Pub. No.: WO2017/176916
PCT Pub. Date: Oct. 12, 2017

(65) Prior Publication Data
US 2019/0151426 A1    May 23, 2019

Related U.S. Application Data

(60) Provisional application No. 62/318,375, filed on Apr. 5, 2016.

(51) Int. Cl.
| | | |
|---|---|---|
| *A61K 39/395* | (2006.01) |
| *A61K 39/00* | (2006.01) |
| *A61K 39/39* | (2006.01) |
| *A61K 9/10* | (2006.01) |
| *A61K 9/00* | (2006.01) |
| *A61K 47/24* | (2006.01) |
| *A61K 9/127* | (2006.01) |
| *A61P 37/06* | (2006.01) |
| *A61K 31/436* | (2006.01) |

(52) U.S. Cl.
CPC ............ *A61K 39/00* (2013.01); *A61K 9/0019* (2013.01); *A61K 9/10* (2013.01); *A61K 9/127* (2013.01); *A61K 31/436* (2013.01); *A61K 39/001* (2013.01); *A61K 39/39* (2013.01); *A61K 47/24* (2013.01); *A61P 37/06* (2018.01); *A61K 2039/545* (2013.01); *A61K 2039/55555* (2013.01); *A61K 2039/577* (2013.01); *A61K 2039/58* (2013.01)

(58) Field of Classification Search
None
See application file for complete search history.

(56) References Cited

U.S. PATENT DOCUMENTS

| | | |
|---|---|---|
| 4,619,794 A | 10/1986 | Hauser |
| 5,536,729 A | 7/1996 | Waranis et al. |
| 2005/0191309 A1 | 9/2005 | Kakkis et al. |
| 2005/0227913 A1 | 10/2005 | Balasubramanian et al. |
| 2007/0009590 A1 | 1/2007 | Purpura et al. |
| 2008/0207756 A1* | 8/2008 | Herweck ............... A61P 39/00 514/560 |
| 2009/0053297 A1 | 2/2009 | Balu-Iyer et al. |
| 2015/0004218 A1 | 1/2015 | Balu-Iyer et al. |
| 2015/0111219 A1 | 4/2015 | Baumeister et al. |

FOREIGN PATENT DOCUMENTS

WO    89/06977 A1    8/1998

OTHER PUBLICATIONS

Bigon et al., Brit. J. Pharmacology, 1979, vol. 67 p. 611-616.*

* cited by examiner

*Primary Examiner* — Yunsoo Kim
(74) *Attorney, Agent, or Firm* — Hodgson Russ LLP

(57) ABSTRACT

Compositions and methods for inducing immune tolerance to proteins and subsequence administration of the proteins are disclosed. Compositions comprise proteins complexed with liposomes comprising PS and PC, wherein at least part of the PS is present as lyso-PS.

15 Claims, 14 Drawing Sheets

A

B

PHOSPHOSERINE CONTAINING COMPOSITIONS FOR IMMUNE TOLERANCE INDUCTION

CROSS-REFERENCE TO RELATED APPLICATIONS

This application claims priority to U.S. Provisional patent application No. 63/318,375, the disclosure of which is incorporated herein by reference.

STATEMENT REGARDING FEDERALLY SPONSORED RESEARCH

This invention was made with government support under contract no. HL-70227 awarded by the National Institutes of Health. The government has certain rights in the invention.

BACKGROUND OF THE DISCLOSURE

Unwanted immune response against therapeutic proteins and self-antigens is a major clinical issue. Similarly, food allergies continue to be a major concern. For example, unwanted immune response against Factor VIII, a replacement therapy used to treat Hemophilia A, a bleeding disorder, elicits antibody response that abrogates the efficacy of the therapy in about 30% patients. Unwanted immune response against self-proteins lead to autoimmune conditions such as multiple sclerosis, diabetes, arthritis etc. Similarly, immune response against food such as wheat, peanut leads to food allergies. There are several approaches that are undertaken to minimize immunogenicity including development of less immunogenic formulation, modifying treatment options, use of steroids and delivery approaches. Each approach has limitations and an effective approach to minimize immunogenicity has not been achieved.

SUMMARY OF THE DISCLOSURE

The present disclosure provides compositions comprising lipid particles which comprise phosphoserine or phosphatidylserine (PS). Some or all of the PS may be present as lysophosphatidylserine (lyso-PS). The present disclosure also provides methods for inducing immune tolerance using such compositions. The disclosure is based on the surprising observation that administration of target proteins complexed to certain lipidic compositions results in immunological hypo responsiveness against the protein for subsequent administration or exposure.

The compositions of the present disclosure comprise complexes of target proteins and liposomes or lipid structures, wherein the liposomes or lipidic structures comprise phosphatidylserine (PS) and phosphatidylcholine (PC). At least some of the PS is present as lyso-PS. For example, all of the PS may be present as lyso-PS. The liposomes may also comprise phosphatidylethanolamine (PE) in addition to PS and PC. The protein can be any target protein.

As an example, the present disclosure provides liposomes which comprise phosphatidylcholine (PC) and lysophosphatidylserine (lyso-PS), wherein the molar ratio of PC to lyso-PS is from 90:10 to 60:40. The acyl chain of the lyso-PS can contain from 14 to 22 carbons. It was observed that a chain length of 18 with one double bond (18:1, oleic acid) was particularly effective in induction of immune tolerance. The acyl chain length of the PC chains can be from 12-22. It was observed that an acyl chain length of 14 (DMPC) was particularly effective in induction of immune tolerance.

In one embodiment, the size of the liposomes comprising PC and lyso-PS is from about 50-150 nm. In one embodiment, about 90% of the liposomes are within a range of 50 to 150 nm. In an embodiment, where PC:lyso-PS (PS is 18:1) was used a molar ratio of 70:30, the size distribution of the particles was found to be: 99% less than 250 nm, 90% less than 160 nm, 75% less than 125 nm, 50% less than 100 nm, 25% less than 70 nm. The mean diameter of the particles can be from 90 to 120 nm. For example, the mean diameter can be from 95 to 110 nm, such as, for example, about 106 nm. The size of the liposomes is for a population that was extruded six times through a 0.2 micron filter. When a PC:PS (double chain, 18:1) was similarly extruded six times through a 0.2 micron filter, the size distribution was: 99% less than 450 nm, 90% less than 280 nm, 75% less than 210 nm, 50% less than 160 nm, and 25% less than 115 nm. When a PC:PS (double chain, 16:0) was similarly extruded six times through a 0.2 micron filter, the size distribution was: 99% less than 310 nm, 90% less than 260 nm, 75% less than 240 nm, 50% less than 215 nm, and 25% less than 200 nm.

The zeta potential of the 30% PS-lyso liposomes (meaning liposomes comprising PC:lyso-PS 70:30) was from about −10 to about −17, while the zeta potential of the 30% PS liposomes (meaning liposomes comprising PC:PS 70:30) was about −24 to about −33. If the size of the 30% PS liposomes was matched to the size of the 30% lyso-PS liposomes (e.g., by filtering the PS liposomes through a 100 nm filter so that both populations had an average size of about 106 nm, the zeta potential of the PS liposomes was found to be from about −17 to about −26. Thus, the PC:lyso-PS liposomes are smaller and surprisingly less negative as compared to corresponding PC:PS liposomes.

An administration strategy disclosed herein is designated as "inverse/reverse vaccination" strategy in which pre-exposure (e.g., immunization) via oral route to particular liposomal compositions (designated here as tolerogenic or priming compositions) complexed to the target protein can lead to hypo-responsiveness to the protein in subsequent challenge with free protein or less tolerogenic, or any other form of the protein (e.g., complexed to any other suitable carrier such as protein or peptide carriers or other carriers such as polyethylene glycol (PEG), surfactants, microspheres etc.) and exposed to the individual via oral or any other route. The induction of immune tolerance is manifested as one or more of the following: down-regulated expression of co-stimulatory signals on dendritic cells, lowered CD4$^+$ T-cell proliferation and/or induced secretion of immuno-regulatory cytokines such as TGF-β and IL-10, and/or reduction in antibody titer.

An administration strategy disclosed herein is designated as "continuous administration strategy" or "continuous mode" where one or more doses of a priming composition are administered on an on-going basis over a period of time. Thus, the regimen of administration can involve administration on a substantially regular basis, which administration may be, for example, daily or weekly, or may be more or less frequent, and may be administered via any route. Such as administration regimen may be carried out for weeks, months, or years. The intervals between the consecutive administrations may be same or different, but will generally maintain the periodicity of administration.

The compositions of this disclosure can be termed as priming compositions. Accordingly, the method of the present invention of providing a therapeutic protein to an individual without eliciting an immune reaction or eliciting a minimal immune response comprises administering a priming composition to an individual, which comprises the protein complexed to liposomes comprising PS, wherein some or all of the PS is present as lyso-PS, and administering to the individual a second composition comprising: i) only the protein (i.e., without liposomes or phospholipids), ii) comprising the protein and liposomes or phospholipids, but not in a complexed form, iii) comprising the protein complexed to liposomes in which the phospholipid composition is different from the phospholipid composition of the priming composition, such as, for example, the composition of the liposomes in the second composition may be free of lyso-PS and optionally, free of PS also, or iv) comprising the protein complexed to some other carrier that is free of lyso-PS and, optionally, free of PS also.

The priming composition may be administered one time or multiple times, and may be administered on an ongoing basis (continuous administration). Similarly, the second composition may be administered one time or multiple times, or an ongoing basis (continuous administration), or administered intermittently as needed. The second composition can administered after allowing a head-start with the first composition, such as after 4-6 weeks of the start of the first composition, or may be administered or started at the same time or within 4-6 weeks of the start of the first composition.

In one embodiment, the priming composition (also referred to as first composition) may be administered on a continuous schedule and the second composition (also referred to herein as a therapeutic composition) may be administered after a time lag after the start of administration of the priming composition, but overlapping the administration schedule of the first composition. Thus, the administration of the second composition may occur concurrently with the administration of the first one, after a period of initial administration of the first composition only.

By using the method of the present disclosure, in the case of a self-antigen or an allergen, the individual will have developed immune tolerance and is not be expected to mount an immune response when exposed to the self-antigen or allergen.

The present compositions and methods are useful for induction of immune tolerance to administered protein, particularly via oral route. The present compositions and methods are also useful for reducing existing antibody titers.

The method of the present invention can be used for individuals who are known to have immunological intolerance to the target protein or to those whose immunological status toward a target protein is unknown. For example, in the case of a therapeutic protein, the present compositions may be used for individuals who are being administered the therapeutic protein but have not previously exhibited an immune intolerance to the protein, or to naïve individuals (i.e., those who have not been previously administered the peptide or protein). Individuals are deemed to not have exhibited immune intolerance to a protein if there are no detectable titers of antibodies to the protein. In the case of a diagnostic protein, the present compositions may be administered to individuals who are known to have had a prior reaction, or to those individuals who have not been administered the target protein previously or have not exhibited an immunological reaction previously. Similarly, for self-antigens or allergens, the present compositions may be administered to those individuals who are known to be immunologically intolerant to the protein or to those whose immunological status is unknown or who are considered to be at risk for developing an allergy to the protein (such as due to carrying a certain gene etc.).

In the present disclosure, it was observed that compositions comprising complexes of proteins with liposomes comprising PC and lyso-PS were effective in inducing immunological tolerance and reducing existing antibody titers relative to complexes of proteins with liposomes comprising PC and PS. In particular, a composition comprising liposomes complexed to an antigen was found to be particularly effective, where the liposomes comprise PC present as DMPC, and PS present as lyso-PS. The effectiveness was more pronounced when the liposomes complexed to proteins (first composition) are administered to an individual for a period of at least 4 weeks, and, without interrupting the schedule of administration of the liposome-protein complex composition of the first composition, a second composition is administered comprising the protein without being complexed to the liposomes of the first composition.

BRIEF DESCRIPTION OF THE FIGURES

FIG. 1 is a representation of continuous mode of administration and shows tolerance induction to FVIII. Male and female knockout mice (n=7 per group) were used. 0.4 μg of FVIII in Tris buffer (150 mM NaCl, 25 mM TRIS, pH 7.0), endotoxin-free was used. The protein to lipid ratio was 1:10,000. Immunizations were done by oral gavage or subcutaneous route. Rechallenge (meaning administration of a second composition) was done by iv route, 24 hours after immunizations. The various treatment groups were: free FVIII, PS FVIII, 15% lyso-PS FVIII (lyso-PS:PS:PC 15:15:70), 30% lyso-PS FVIII (lyso-PS:PC 30:70).

FIG. 2 shows in A) and B) the results of oral administration described in FIG. 1. Only lyso-PS induces tolerance when administered orally.

FIG. 3 shows in A) and B) the results of subcutaneous administration described in FIG. 1. Both PS and lyso-PS are able to induce tolerance when administered subcutaneously. Asterisks indicate statistically significant differences.

FIG. 4 is a representation of oral tolerance. Male and female FVIII KO mice (n=7 were used) were used. 0.4 μg of FVIII in Tris buffer (150 mM NaCl, 25 mM TRIS, pH 7.0), endotoxin-free was used. The protein to lipid ratio was 1:10,000. Immunizations were done by oral gavage. Rechallenge was done via tail vein. The various treatment groups were: buffer, free FVIII, PS FVIII, and 30% Lyso-PS FVIII.

FIG. 5 shows in A) and B) the oral tolerance results from administration described in FIG. 4.

FIG. 6 shows the reversal of established titers via oral tolerance. Male and female KO mice (n=7 per group) were used. 0.4 μg of FVIII in Tris buffer (150 mM NaCl, 25 mM TRIS, pH 7.0), endotoxin-free was used. The protein to lipid ratio was 1:10,000. Inductions were done via subcutaneous route. Immunizations were done by oral gavage. The various treatment groups were: buffer, free FVIII, PS FVIII, and Lyso-PS FVIII.

FIG. 7 shows the results of reversal of established titers via oral tolerance described in FIG. 6.

FIG. 8 shows lyso-PS antigen specificity via subcutaneous administration. Male and female GFP-FoxP3 HA mice (n=18 per group) were used. 0.4 μg of FVIII in Tris buffer (150 mM NaCl, 25 mM TRIS, pH 7.0), endotoxin-free was used. The protein to lipid ratio was 1:10,000. Immunizations and rechallenge were done via subcutaneous administration. 6 animals per group were sacrificed at baseline. 6 animals per group received FVIII rechallenge, while the remaining 6 animals received ovalbumin rechallenge. The various treatment groups were free FVIII and Lyso-PS FVIII.

FIG. 9 shows the results of lyso-PS antigen specificity from subcutaneous administration described in FIG. 8. A) shows baseline titer data. B) shows terminal anti-FVIII titer data. C) shows terminal anti-OVA IgG data.

FIG. 10 shows lyso-PS antigen specificity via oral gavage. Male and female GFP-FoxP3 HA mice (n=12 per group) were used. 0.4 µg of FVIII in Tris buffer (150 mM NaCl, 25 mM TRIS, pH 7.0), endotoxin-free was used. The protein to lipid ratio was 1:10,000. Immunizations were done via oral gavage. Rechallenge was done via intravenous administration. 6 animals per group received FVIII rechallenge, while other 6 animals per group received ovalbumin rechallenge. The various treatment groups were: free FVIII, lyso-PS FVIII, and buffer.

FIG. 11 shows the results of lyso-PS antigen specificity via oral gavage described in FIG. 10. A) shows terminal anti-FVIII titer data. B) shows terminal anti-OVA IgG data.

Figure 16:
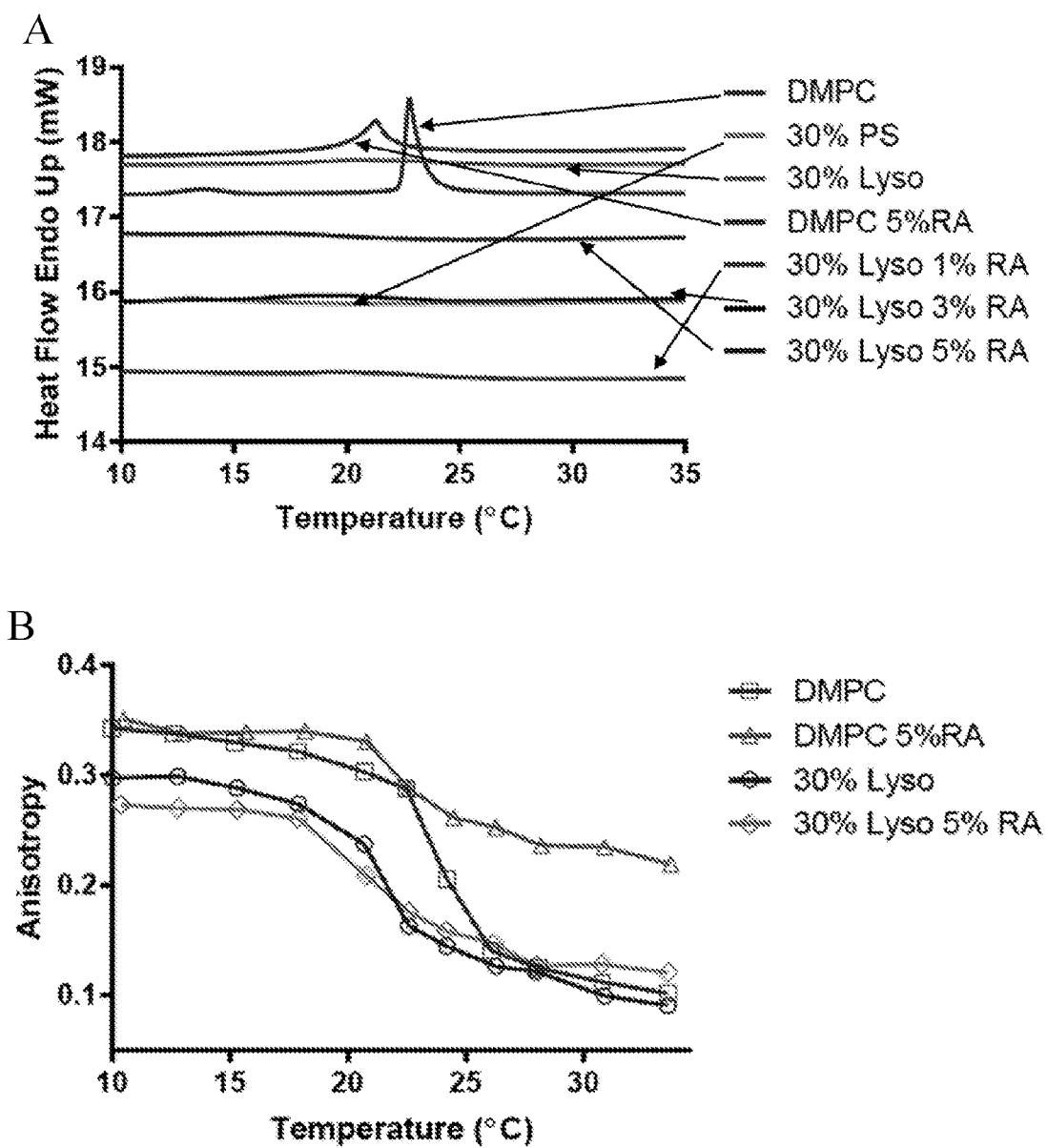
Figure 16:
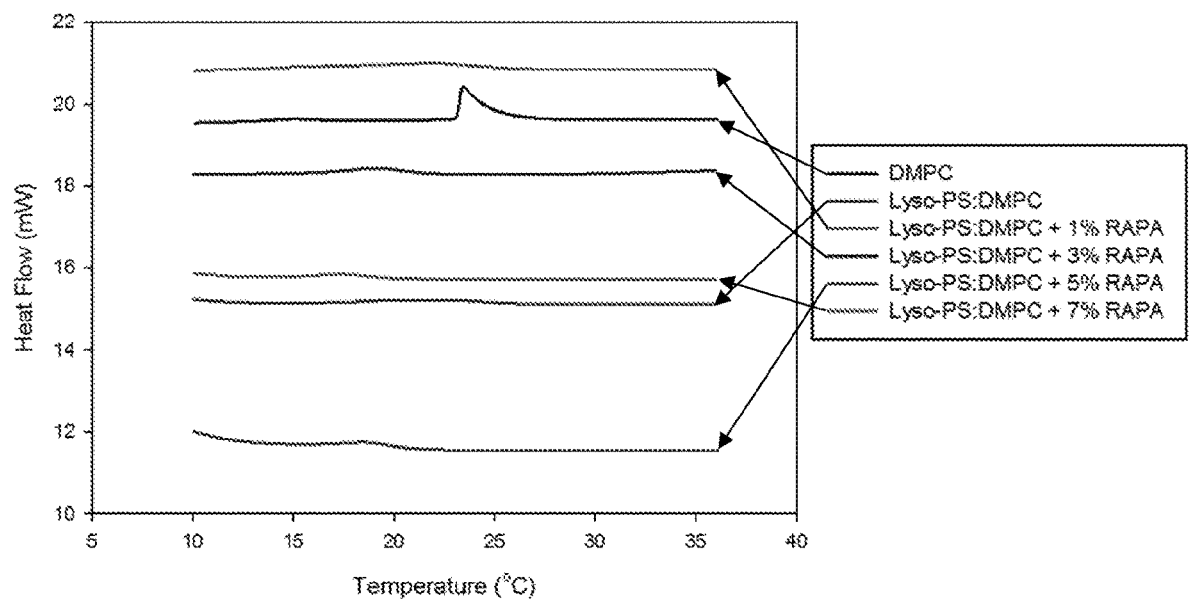

FIG. 16 shows A) a DSC thermogram of lyso:RA. B) Fluorescence polarization of liposomes containing 5% RA. C) DSC thermogram of rapamycin loaded in lyso-PS.

Figure 17:
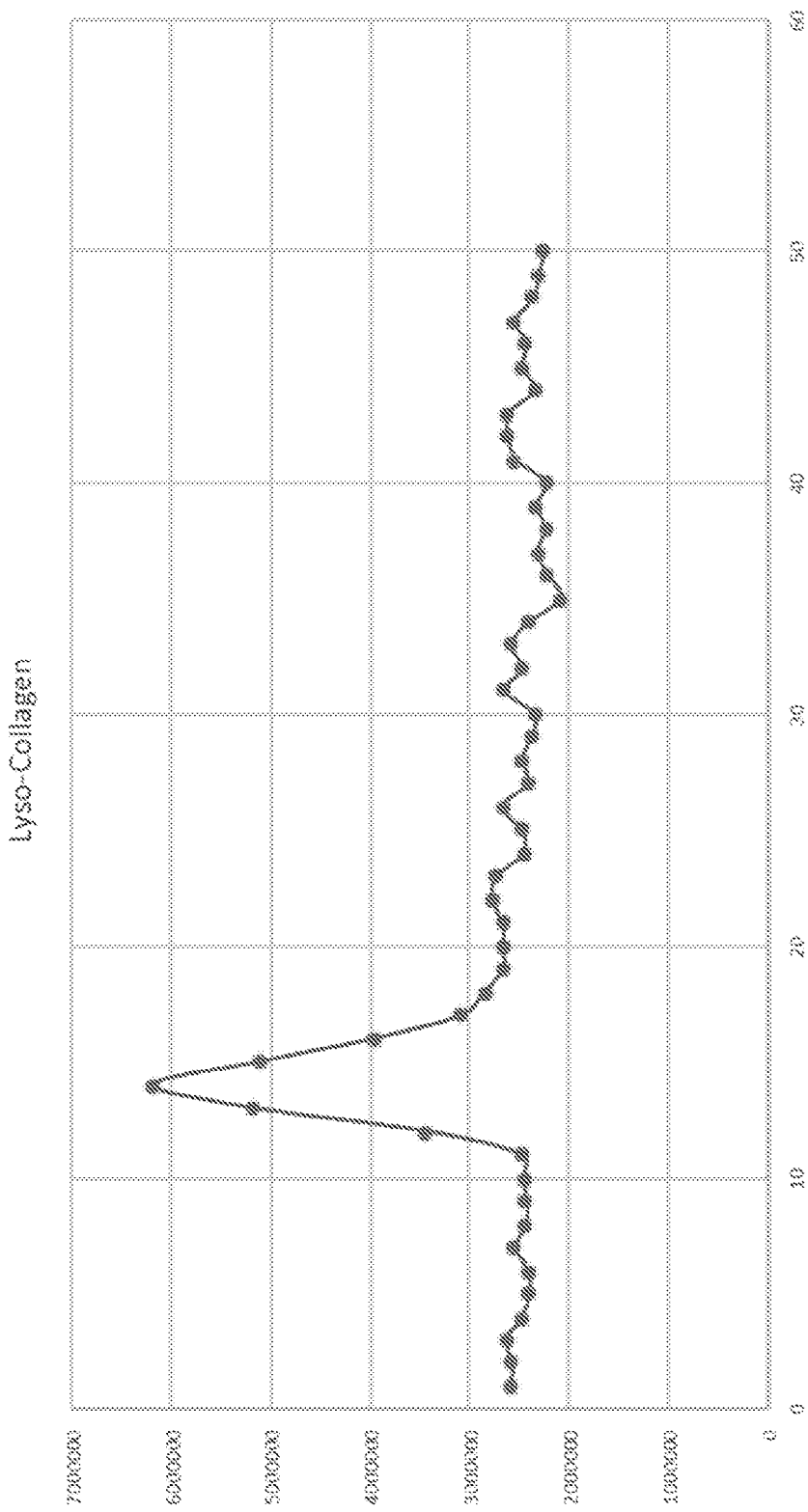

FIG. 17 shows the association efficiency of lyso-collagen (lyso-PS liposomes complexed with collagen) via a BCA assay. Efficiency was ~62%.

Figure 18:
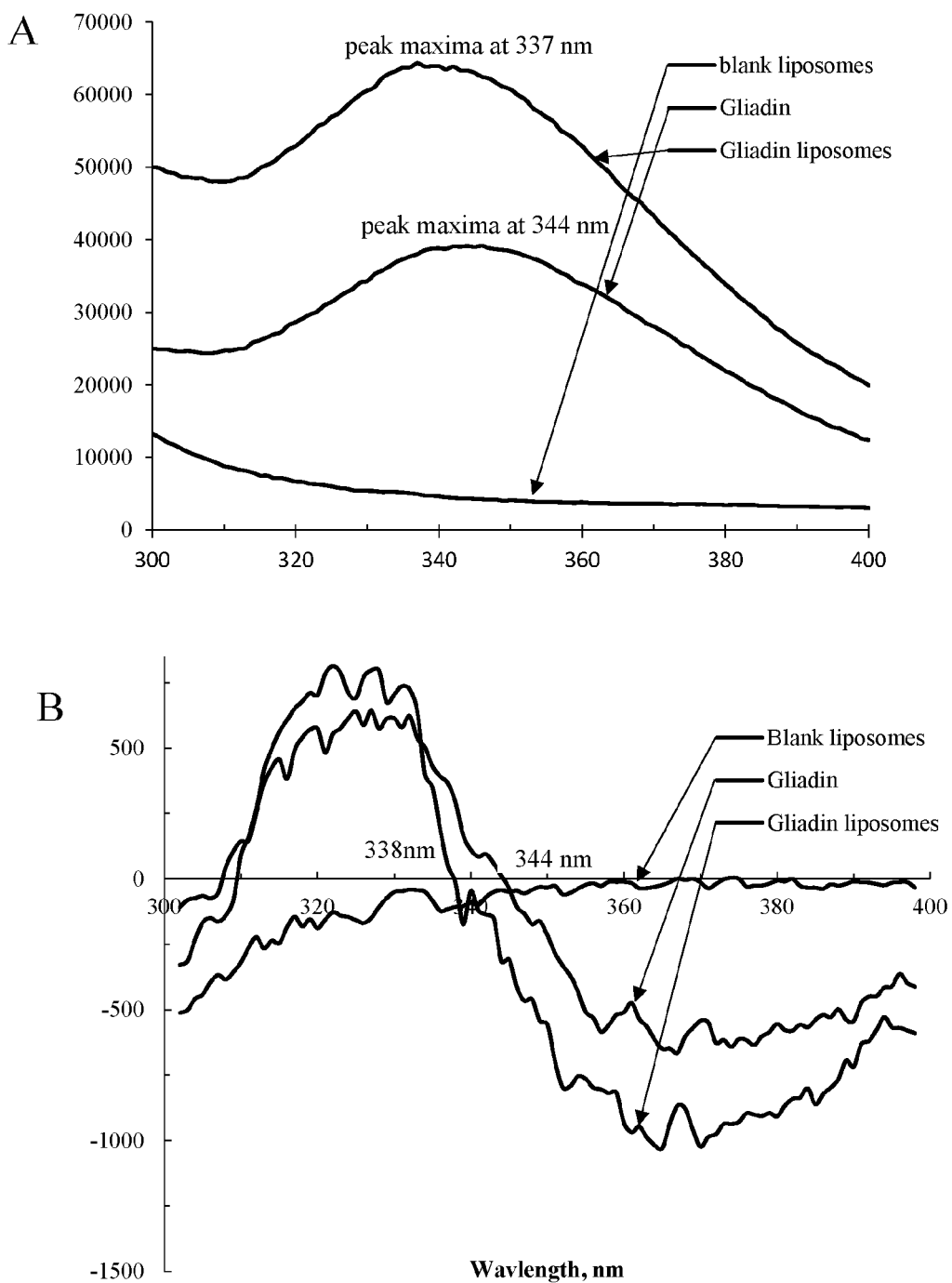

FIG. 18 shows A) fluorescence of lyso-PS liposomes complexed with gliadin. B) First derivative of the spectrum shown in A).

DETAILED DESCRIPTION OF THE DISCLOSURE

The present invention provides compositions and methods for inducing immune tolerance toward a protein. The protein may be a therapeutic protein, a diagnostic protein, a self-antigen or an allergen. For example, the method can be used for individuals who are on a therapeutic protein therapy and may or may not have previously exhibited an immune intolerance. It can also be administered to individuals who are to start on a therapeutic regimen for a particular therapeutic protein. Similarly, the method can be used for individuals who may have exhibited an allergic reaction to a diagnostic protein or to an individual as a prophylactic measure before the diagnostic protein is administered to an individual who has never encountered the protein. Further, it can be administered to an individual who has exhibited an immunological reaction to a self-antigen or allergen or who may be at risk of exhibiting a reaction to such proteins.

The present compositions comprise proteins complexed to liposomes. The liposomes may be referred to as the [antigen]-PS. As used herein, the term protein-PS means the protein is complexed to liposomes containing PS and PC. For example, complexes of FVIII with liposomes comprising PS and PC may be referred to herein as FVIII-PS and the complexes of FVIII with liposomes comprising lyso-PS and PC may be referred to herein as FVIII-lyso-PS and so on.

The term "target protein" as used herein means any protein to which an immunological hypo responsiveness is desired. For example, a target protein may be a therapeutic protein, a diagnostic protein, a self-antigen, a neo-antigen, an allergen or the like.

By "specific" immunological response is meant that an immune response to non-relevant proteins (proteins that were not complexed to the liposomes of the priming composition) is not affected.

By "administered" or "administration" is meant that the protein or peptide is delivered to the individual or introduced into the individual's body by any means or route of delivery.

By "inhibitory" titers or antibodies in reference to a protein or antigen is meant specific antibodies that inhibit the biological activity of the protein or antigen. For example, inhibitory titers in reference to FVIII can be determined by measuring interference with blood clotting time. Total titers, in contrast refers to all the antibodies (such as IgG, IgM etc.)

By "lipidic structures" is meant liposomes and other structures such as micellar structures, liposomes, cochleates, molecular assemblies and the like.

The term "lyso" when used herein in conjunction with a phospholipid means that the glycerol part of the molecule has only one acyl chain instead of two. For example, lyso-PS has only one acyl chain as compared to PS which has two acyl chains.

By reference to protein complexed to liposomes or liposomes complexed to protein is meant that the protein may be associated with the particle in one or more of the following configurations including location in the lumen of the particle, partly or fully intercalated in the bilayer or bound or adsorbed to the surface of the particle. As examples, data is provided herein for liposomes-protein complexes for several proteins including FVIII, insulin, acid alpha glucosidase (GAA), myelin oligodendrocyte glycoprotein (MOG) peptide (35-55), ovalbumin (OVA), gliadin, collagen, adeno associated virus (AAV) capsid protein.

Liposomes are also referred to herein as lipidic nanoparticles, or nanoparticles. The phospholipids for preparing the liposomes can be obtained from any available source such as plant or animal. The phospholipids are commercially available or can be synthesized by known methods. For example, PS can be obtained from porcine brain PS or plant-based soy (e.g., soya bean) PS. Lyso-PS is also available commercially. For purposes of this description, while examples of protein complexes or induction of immune tolerance may refer to specific proteins, it is equally applicable to other proteins.

The liposomes and other lipid structures comprise PC and PS, some or all of which may be in the form of lyso-PS. The liposomes or other lipid structures may contain PS (or lyso-PS) and PC as the only phospholipids. The PS or lyso-PS may be in a range of from 10% to 50% of the total phospholipids in the bilayer. From 1 to 100% (and all values and ranges therebetween) of the PS may be in the form of lyso PS. For example, the liposomes may have PC:lyso-PS as 90:10, 80:20, 70:30, 60:40, or 50:50 molar ratios. In an example, the lyso-PS can be from 15 to 50 molar %, the remaining phospholipids being PC. For example, the lyso-PS can be from 15 to 30%. Whenever a range is mentioned in this disclosure, all values within that range are also included. In one example, only the PS (some or all) is in the form of lyso-PS, while all of PC has two acyl chains. All ratios of phospholipids in this disclosure are molar ratios.

In one example, the lipidic structures, such as liposomes, in which from 0 to 100% of the PS is present as lyso PS, further comprise retinoid acid and/or rapamycin. Thus, the lipidic structures can comprise PS (some or all of which can be lyso-PS), PC and retinoid acid and/or rapamycin. The amount of retinoic acid can be from 0.1 mol % to 10 mol % and all percentage values to the tenth decimal place therebetween. The amount of rapamycin can be 0.1 mol % to 10 mol % and all percentage values to the tenth decimal place therebetween.

PS and PC may independently have from 1-22 carbon atoms in each of the acyl chain. For example, when the carbon atom is 0 for PS, the molecule is O-Phospho-L-Serine (OPLS). The acyl chains have 1 to 22, 2 to 22, 6 to 22, or 14 to 22 carbons (and all integer number of carbons and ranges therebetween). The acyl chains can be saturated or unsaturated. The PC or PS may have one or two acyl chains. Thus, the PS or PC may be lyso-PS or lyso-PC.

In an example, at least some of the PS is lyso PS, but the PC is not lyso-PC. In this example, all of the PC has two acyl chains and at least some PS has only one acyl chain. For example, the PC:PS ratio is 90:10 to 60:40, and all of the PS is lyso-PS. For example, the PC:lyso PS may be 85:15 to 65:35. In an example, the ratio of PC:lyso-PS may be 70:30. In an example, the lyso-PS is from 15 to 50% or 15 to 35% with the remaining phospholipids being PC. The lyso-PS and PC may be the only phospholipids present in the bilayer of the liposomes. The total lyso-phospholipid in the liposomes is preferably less than 50% of the total phospholipid because if the lyso-phospholipid percentage is higher than 50%, the liposomes are not stable.

The lyso PS acyl chain may be unsaturated. It can be from 14 to 22 carbons. It should have at least one double bond. For example, it can be 18:1. It may have 2 or 3 double bonds, although the stability of the liposomes was found to be the better with a single double bond than with 2 or 3 double bonds. However, at least one double bond was found to be necessary for enhanced effectiveness.

The acyl chains of the PC may be from 12 to 22 carbons. The acyl chains are preferably both of the same length and saturated. It was observed that a chain length of 14 (C14:0, dimyristoyl-sn-glycero-3 phosphatidylcholine (DMPC)) was particularly effective in providing stability to the liposomes. When a chain length of 18 (1,2-Distearoyl-sn-glycero-3-phosphocholine (DSPC)) was used, it was found to be not as effective as DMPC.

The present liposomes may further comprise additional phospholipids. For example, any of the liposomes described herein may have phosphatidylethanolamine. The amount of PS, some or all of which may be lyso-PS, may be 0 to 30 mol %, the amount of PC may be 0-30 mol %, and the remaining may be PE. For example, PS, some or all of which may be lyso-PS, may be from 1 to 30 mol %, PC may be from 1 to 30 mol % and the remaining can be PE.

The liposomes comprising lyso PS as described herein were found to be smaller than the liposomes comprising only PS (without any lyso PS). For example, after filtration through a 0.2 micron cutoff filter, the size of the lyso-PS containing liposomes (liposomes containing lyso PS and PC) was about 50-150 nm (about 90% of the liposomes), while the size of PS containing liposomes (PS+PC) was about 200-400 nm (about 90% of the population). It was surprising that the even though the lyso PS liposomes are smaller than the PS liposomes, the charge is not as negative. The zeta potential for the lyso PS liposomes is −10 to −17 compared to a zeta potential of −24 to −33 for PS liposomes, and −17 to −26 for size matched liposomes. The less negative charge on the lyso-PS liposomes may enable increased loading of proteins. For example, for PS liposomes, a typical protein:lipid ratio is 1:10,000 molar ratio, but for lyso-PS liposomes, the protein could be loaded and used at at least up to 1:5,000 molar ratio. Proteins can be loaded on to the lyso-liposomes at molar ratios from 1:1,000 to 1:10,000 (and all ratios therebetween).

In an aspect, the present disclosure provides compositions comprising liposomes. For example, the composition may comprise a plurality of liposomes described herein in a suitable carrier. A suitable carrier may be a buffer or other pharmaceutical carriers or additives, excipients, stabilizers, or a combination thereof. For example, the liposomes may be formulated in sugars, starches, cetyl alcohol, cellulose, powdered tragacanth, malt, gelatin, talc, oils, glycols, glycerol monooleate, polyols, polyethylene glycol, ethyl alcohol, additional emulsifiers and the like. Examples of pharmaceutically acceptable carriers, excipients, and stabilizers can be found in Remington: The Science and Practice of Pharmacy (2005) 21st Edition, Philadelphia, Pa. Lippincott Williams & Wilkins.

The present priming composition can be formulated for oral delivery. The composition may be directly delivered to the desired location in the gastrointestinal tract using gavage. Or they can be formulated in the form of liquid, suspensions, tablets (including enteric coated tablets), gels, capsules, powder or any other form that can be ingested. Formulations can include pharmaceutical carriers known to be used for oral formulations. The formulations can be pediatric formulations, which can include various flavors and the like.

The present compositions are useful for not only inducing immune tolerance, but are also useful for reducing antibody titers of existing antibodies. It was observed that while PS liposomes (where PS contained two acyl chains) were effective when administered subcutaneously in the induction of immune tolerance, they were not effective if administered orally. However, liposomes containing lyso PS were effective when used orally. This was surprising.

In one aspect, this disclosure provides a method for inducing immune tolerance, wherein a first composition (priming composition) is administered on a continuous basis, where one or more doses of a priming composition are administered on an on-going basis over a period of time, and a second composition (therapeutic) is administered on an on-going basis or as needed overlapping the administration regimen of the first composition. Thus, the regimen of administration of the first composition can involve administration on a substantially regular basis, which administration may be, for example, daily or weekly, or another frequency, and may be administered via any route. In one embodiment, the administration is via an oral route. Such as administration regimen may be carried out for weeks, months, or years. The intervals between the consecutive administrations may be same or different, but will generally maintain the periodicity of administration.

In one aspect, this disclosure provides a method for inducing immune tolerance to a target protein in an individual comprising providing to the individual a first regimen of multiple administrations of a priming composition (first composition) over a period of time, for example extending beyond at least 4 weeks, wherein the priming composition comprises liposomes or other lipidic particles comprising PC (such as DMPC) and PS, wherein some or all of the PS is present as lyso-PS. This disclosure also provides a method of delivering a therapeutic protein to an individual comprising providing to the individual a first regimen of multiple administrations of a priming composition (first composition) over a period of time, for example extending beyond at least 4 weeks, wherein the priming composition comprises liposomes or other lipidic particles comprising PC (such as DMPC) and PS, wherein some or all of the PS is present as lyso-PS, and at any time, while continuing the first regimen, providing to the individual a second regimen of one or more administrations of a second composition comprising the protein (in a therapeutically effective amount) free of liposomes, or comprising the protein and liposomes but not in a complexed form, or comprising the protein complexed to liposomes which do not contain PS or lyso-PS, or comprising the protein complexed to some other carriers which do not contain PS or lyso PS, whereby there is no significant immunological response, or the immunological response against the protein is lower than with a priming composition comprising PS-liposomes (no lyso-PS) or with free protein. The second composition may be started after 4-6 weeks of the first composition or may be started before that. Immunological response may be measured as specific antibody titers. Thus, no significant immunological response means no antibodies directed to the protein are detected in the blood. When the priming composition is administered regularly, and a second composition administration is started without stopping or interrupting the administration regimen of the priming composition, the overall schedule may be referred to as a continuous administration schedule. For example, the first composition may be administered for about 6 weeks (on a weekly basis) and continued thereafter for weeks, months or years, and the administration of the second composition can be started about 4 to 6 weeks after the start of the first regimen and can be continued as needed over weeks, months or years. The administration regimen of the second composition overlaps the regimen of the first composition. By overlap is meant that the administrations regimens overlap; however, the two compositions need not be administered at the same time. The administration of the second composition in this disclosure may be referred to as "challenge or re-challenge". Once the second composition is started, both the first and the second compositions can be continued to be administered as long as the second therapeutic composition is required. The administrations of the first composition and the second composition can be done at suitable frequencies. For example, daily, weekly, biweekly, etc., or any frequency in between or beyond.

The disclosure also provides a method for providing a therapeutic protein to an individual without eliciting an immune reaction or eliciting a minimal immune response, or eliciting an immune response that is lower than the response for PC:PS liposomes, said method comprising administering a priming composition to an individual, which comprises the protein complexed to liposomes comprising lyso-PS, and while continuing the administration regimen of the first composition, administering to the individual a second composition comprising only the protein (i.e., without liposomes or phospholipids) or comprising the protein and liposomes or phospholipids, but not in a complexed form, or comprising the protein complexed to liposomes in which the phospholipid composition is different from the phospholipid composition of the priming composition. For example, the composition of the liposomes in the second composition may be free of lyso-PS and optionally, free of PS also.

In one embodiment, the present method comprises administering to an individual a first composition (also referred to herein as a priming composition) which can comprise one or more administrations or doses comprising a target protein (such as a therapeutic or diagnostic protein, a self-antigen, or an allergen) complexed with liposomes comprising PS and PC (referred to herein as PS liposomes). At least some of the PS may be present as lyso-PS. For example, all of the PS may be present as lyso-PS. The first administration can be followed up with one or more administrations of the priming composition. The priming compositions can be administered 1 time a week or more times a week. For example, the priming composition can be administered once a week or two to six times a week or may be administered daily. Administration can be carried out for 1, 2, 3, 4, 5, 6 or more weeks, and then stopped. After a suitable period of time allowing immune tolerance to develop (such as, for example, at least 4 days after the last primer), the individual can be administered a second composition (one or more administrations) comprising the protein or peptide in the free form, complexed to liposomes or lipidic structures having a different composition than the primary composition, or complexed (covalently or noncovalently) to PEG, or surfactants or microspheres and the like.

For example, the individual may be administered the second composition after 4 to 30 days, including all integer number of days and ranges therebetween, of the last priming composition administration. For example, the individual is administered the second composition after 5, 6, 7, 8, 9, 10, 11, 12, 13, 14 and 15 days of the last of the last priming composition administration. Less immunogenic formulations are disclosed in U.S. patent and patent application nos. U.S. Pat. Nos. 7,351,688; 7,875,288; 7,875,289; 7,625,584; 20090053297; PCT/US2010/041196, the relevant disclosures of which are incorporated herein by reference.

This invention can be used for any individual (e.g., a human or a non-human mammal). For example, the present compositions can be administered to an individual who has previously been administered the protein or peptide but has not previously developed immune intolerance. The individual may or may not be showing indications of a recent immune intolerance. It is also useful for administration to naïve individuals (i.e., those individuals who have not been administered the protein or peptide previously). Immune intolerance as used herein means the individual should have measurable (by standard methods such as ELISA or activity assays) antibody production. Conversely, a lack of immune intolerance means the individual has no measurable antibodies. The antibodies may be measured after exposure to or administration of free form of the protein after an individual has been "tolerized". The term tolerized as used herein means administration of one or more doses of priming composition and a suitable length of time (such as from 4 to 30 days) for an individual to develop immune tolerance. Development of immune tolerance against the target protein can also be identified by determining down-regulated expression of co-stimulatory signals on dendritic cells, lowered $CD4^+$ T-cell proliferation, and induced secretion of immuno-regulatory cytokines TGF-β and IL-10. One or more of these identifiers can be evaluated in culture conditions. The development of immune tolerance is specific to the protein against which tolerance is induced (i.e., the protein complexed with the liposomes of the priming composition).

The priming composition may be administered for up to several weeks. As an example, the priming composition may be administered for 4 weeks. The frequency of oral administration of the priming composition (such as protein-lyso PS liposomes) can be once-a-week or more for four weeks. More doses of protein-lyso PS can also be used.

The priming compositions and the second composition may independently be delivered by any standard route such as intravenous, intramuscular, intraperitoneal, mucosal, subcutaneous, transdermal, intradermal, oral, and the like.

The phospholipid composition of the liposomes or lipidic structures in the second composition (which may be a therapeutic composition) may be the same or different from the phospholipid composition of the liposomes of the first composition (which is a priming composition).

The present compositions can be used for not only inducing immunological tolerance specific to an antigen, but also to reverse established antibodies. For example if an individual is showing high titers to an antigen, administration of the present lyso-PS liposomes can be carried out to effect reduction in the antibody titers. Reversal of established antibodies was observed only with lyso-PS liposomes, and not with PS liposomes. This was surprising. The buffer treated group received four injections of FVIII similar to other groups but during immunization, they received buffer. We observed reduction in titers for Lyso PS group that is lower than this buffer control group suggesting that Lyso group not only prevented formation of new antibodies but reduced existing antibodies. Preferably the oral lyso PS with antigen treatment would continue when the re-challenge with free antigen resumes.

The present compositions may be administered to individuals who are in need of inducing immunological tolerance. These may be individuals who have never been exposed to the antigen, or may be administered to individuals who exhibit antibodies against the antigen. For example, the individuals may be exhibiting high titers of antibodies against the antigen. The present compositions can not only induce immunological tolerance, but can also reduce existing antibodies. In one embodiment, an individual may be first tested for the presence of specific antibodies to an antigen (such as by an immunoassay, such as ELISA), and if the individual is found to exhibit antibody titers, then the individual may be administered a regimen of the antigen incorporated in lyso-PS liposomes.

A suitable regimen of an antigen complexed to lyso-PS liposomes typically comprises multiple administrations (such as weekly administrations, e.g., one a week for 4 weeks) of the antigen-lyso-PS liposomes, which can then be followed by administration of the antigen not complexed to lyso-PS liposomes. A composition in which the antigen is not complexed to lyso-PS liposomes may be free of liposomes, or may comprise the antigen complexed to liposomes which do not contain lyso-PS, or may comprise liposomes but not complexed to the antigen.

In the present studies, only PS, but not charge matched PG or PC induced hypo-responsiveness following its pre exposure and re-challenge with free protein. Thus, presence of PS is critical for the ability of lipid-based nanoparticles to induce tolerance. We also show that administration of anti-TIM-4 antibody in the presence of FVIII reversed the tolerizing effect of PS suggesting that TIM-4 receptor is involved in tolerance. Further, a single chain phospholipid was found to be useful only with respect to PS. Lyso PC did not increase the production of regulatory cytokine and therefore, lyso-PC is preferably not used. We found that only presence of 18:1 lyso-PS, but not 16:0 decreased the size of the liposomes and thus the chain length and unsaturation is critical for the size reduction. Because size of the 18:1 lyso containing nanoparticles was smaller, we expected that lyso 18:1 would increase the charge density of the nanoparticles compared to conventional PS liposomes. Surprisingly, nanoparticles containing 18:1 lyso PS showed less negative charge compared to other controls and did not increase charge density. The present data also shows that pre exposure via oral route of protein complexed to 18:1 lyso-PS liposomes, induced better immunological tolerance compared to proteins complexed to 18:1 PS liposomes (two chains in PS), and compared to natural PS composition (e.g., from brain, which is mainly a mix of 18:1 and 18:0). Thus, single chain with unsaturation appears to be critical but is not driven by charge density as expected. The biophysical characteristics include size in the range of 50-150 nm, with zeta potential of about −10 to −15 mV. The conventional PS liposomes containing double chain PS showed mean size of 200 nm with zeta potential of −30 mV where double chain conventional liposomes extruded to size in the range of 50-150 nm showed zeta potential around −20 mV. Further comparison of double chain PS to lyso PS, two different routes of administration of the first composition, sc and oral route were tested. Both lyso-PS and PS liposomes induced tolerance when given via sc route but lyso PS was more effective via oral route compared to conventional PS liposomes.

Further, the duration of oral administration continuous compared to four weekly administration was also attempted. Following sc administration, four weekly injection was sufficient to induce hypo-responsiveness but following oral route four weekly injections were ineffective. The continuous oral feeding was very effective for lyso PS 18:1 nanoparticles and majority of the animals did not show any measurable titers.

Some examples of specific embodiments are provided below.

A composition comprising a plurality of liposomes, wherein the liposomes comprise phosphatidylcholine (PC) and lysophosphatidylserine (lyso-PS), wherein the ratio of PC to lyso-PS is from 90:10 to 60:40. The acyl chain of the lyso-PS can be oleic acid (18:1). The ratio of PC to lyso-PS can be from 85:15 to 70:30. The PC may be present as dimyristoyl-sn-glycero-3 phosphatidylcholine (DMPC). The size of the liposomes is from 80 to 150 nm (90% of the population). The zeta potential of the liposomes is from −10 to −15. The liposomes may be complexed to an antigenic polypeptide, such as, for example, FVIII, GAA, MOG peptide, gliadin, insulin, AAV capsid protein, other capsid proteins, collagen and the like. The PC and lyso-PS may be the only phospholipids present in the bilayer of the liposome. The composition may further comprise retinoic acid wherein the ratio of PC, PS and retinoic acid is 70:20:10 to 70:29:1, or rapamycin wherein the ratio of PC, PS and rapamycin is 70:20:10 to 70:29:1.

A method for inducing immune tolerance to a target protein in an individual comprising: a) providing to the individual a first regimen of multiple administrations over a period of at least 6 weeks of a first composition comprising the liposomes of claim 1 complexed to a target protein; and b) while continuing the first regimen, providing to the individual a second regimen of one or more administrations of a second composition comprising the antigen free of liposomes. The second regimen can be started at least 4 weeks after the start of the first regimen. The liposomes of the first composition can comprise PC:lyso-PS in a ratio of 85:15 to 70:30. All of PC can be is dimyristoyl-sn-glycero-3 phosphatidylcholine (DMPC). The acyl chain in lyso-PS is oleic acid. The target protein can be a therapeutic protein, a diagnostic protein, a self-antigen, a neo antigen, or an allergen. The regimen for administration for the first composition can continue over at least 9 weeks before the start of the second regimen. Multiple administration of the first composition can be carried out weekly.

A method for inducing immune tolerance to a target protein in an individual comprising: a) providing to the individual a first regimen of multiple administrations over a period of at least 6 weeks of a first composition comprising the liposomes of claim 1 complexed to a target protein; and b) while continuing the first regimen, providing to the individual a second regimen of one or more administrations of a second composition comprising the antigen and liposomes which do not contain lyso-PS, wherein the second regimen is started at least 4 weeks after the start of the first regimen.

The following example is provided for illustrative purposes and not intended to be limiting.

Example 1

This example describes PS containing liposomes with phosphatidyl ethanolamine. PS/PC liposomes reduce immunogenicity of therapeutic proteins as the result of PS group's exposure on the outside. In this study, PE is incorporated in the liposomes' formulation to determine if it increases the exposure of PS.

PC and PE have a net neutral charge in their head groups while PS has a net negative charge. Therefore, if there is more PS head groups exposing on the outside of the liposomes, their exterior would be more negatively charged. To determine the charge on the surface of PS/PC/PE liposomes, a zeta potential study was conducted. The data shows that the charge on PS/PC/PE liposomes' surface decrease as a function of PE (Table 1).

TABLE 1

|  | 30PS - 70PC - 0PE | 29PS - 68PC - 3PE | 26PS - 62PC - 12PE |
|---|---|---|---|
| Average Zeta Potential (mV) | −17.1 | −20.4 | −27.4 |

The table shows that the particles are stable. Exposure of PS in the outer membrane leaflet is important for induction of immune tolerance.

Since PS is negatively charged, it provides a charge to the lipidic particle. The range of zeta potential for the present particles may be from −1 to −35. For example, the zeta potential may be from −15 to −30.

Example 2

This example provides a description of the methods used in the following examples.

Methods

Materials.

Dimyristoylphosphatidylcholine (DMPC), porcine brain phosphatidylserine (PS), and Lyso-phosphatidylserine (Lyso-PS) were purchased from Avanti Polar Lipids (Alabaster, Ala.). Full length recombinant human factor VIII (FVIII) was a generous gift from the Hemophilia Center of Western New York (Buffalo, N.Y.). Recombinant human acid alpha-glucosidase (rhGAA) was provided by Genzyme Corporation (Cambridge, Mass.). Mouse MOG35-55 was purchased from AnaSpec Inc. (Fremont, Calif.). All solvents and buffer salts as well as incomplete Freund's adjuvant and *Mycobacterium tuberculosis* H37RA were obtained from Fisher Scientific (Fairlawn, N.J.). Pertussis toxin (PTX) was purchased from List Biological Laboratories Inc. (Campbell, Calif.). Murine TIM-4 antibody was purchased from BioLegend (San Diego, Calif.). Anti-FVIII monoclonal antibody ESH8 was obtained from American Diagnostica Inc. (Greenwich, Conn.). Activated partial thromboplastin time (aPTT) reagents were purchased from Diagnostica Stago (Parsippany, N.J.). Normal pooled and deficient human plasma were purchased from Precision Biologic (Dartmouth, Canada). Alkaline phosphatase-conjugated goat anti-mouse Ig antibody was purchased from Southern Biotech (Birmingham, Ala.). p-nitrophenylphosphate (pNPP) substrate system was purchased from KPL Inc. (Gaithersburg, Md.). Horseradish peroxidase-conjugated goat anti-mouse IgG antibody and 3,3',5,5'-tetramethylbenzidine substrate (TMB) were purchased from Sigma Aldrich (St. Louis, Mo.). Endosafe Endochrome-K® Kit was purchased from Charles River Laboratories (Charleston, S.C.). NUNC MaxiSorp 96 well plates were purchased from Thermo Scientific (Waltham, Mass.).

Animals. FVIII Knockout Mice:

A colony of hemophilic mice with a targeted deletion in the exon 16 of the Factor VIII gene as well as Green Fluorescent Protein (GFP) knocked-in to the FoxP3 gene (termed GFP-FoxP3 HA mice) was maintained on-site. This animal model allows for the ease of tracking the expression of FoxP3$^+$ regulatory T cells ($T_{regs}$) due to the GFP being knocked into the FoxP3 gene in the disease model. All animal experiments were conducted under approval and following the guidelines of the Institutional Animal Care and Use Committee (IACUC) of the University at Buffalo.

Preparation of Liposomes.

PS and Lyso-PS liposomes were prepared at a 30:70 molar ratio of PS or Lyso-PS to DMPC. After rehydration with Tris buffer, liposomes were extruded multiple times through double stacked 200 nm polycarbonate membranes using a high pressure extruder. The size of the liposomes was confirmed using a NICOMP Model CW380 particle size analyzer from Particle Sizing Systems (Port Richey, Fla.). The lipid content was confirmed using a phosphate assay. The protein to lipid ratio used was 1:10,000 for experiments using protein antigens. The antigens were associated with the liposomes by incubation at 37° C. for 30 minutes. All formulations were tested for endotoxin level using a limulus amebocyte assay from Charles River Laboratories (Charleston, S.C.) and confirmed to be endotoxin negative before injection.

Determination of Anti-Drug Antibodies.

Total anti-protein antibody titers were determined by ELISA. Anti-FVIII inhibitory titers were analyzed by an aPTT assay following Nijmegen's modified Bethesda assay and expressed in Bethesda units (BU/mL). Total anti-Ova IgG titers were determined by ELISA. 96-well plates were coated with 2 μg/mL of Ova in 1× phosphate-buffered saline (PBS) overnight at 4° C. The following day, plates were washed and blocked with 5% bovine serum albumin in PBS for 1 hour at 37° C. The plates were then washed and 3-fold serial dilution of sample plasma were added to the plate and incubated for 1 hour at room temperature. Titers were determined using a statistically significant cutoff from sham-treated animals.

Statistical Analysis.

One-way ANOVA followed by Tukey's post-hoc analysis or unpaired two sample t-test were performed as indicated using GraphPad Prism (La Jolla, Calif.). P values<0.05 were considered statistically significant.

Oral Tolerance.

Age-match and gender-match HA mice was used with n=7 per treatment group. Each animal received 0.4 μg FVIII in Tris buffer (150 mM NaCl, 25 mM Tris, pH 7.0). A 1:10000 protein:lipid molar ratio was used. Animals received oral administration of 0.4 μg FVIII in the presence and absence of various liposome formulation from weeks 1-9, and received an IV injection via the tail vein of 0.4 μg FVIII 24 hours after oral administration on weeks 6-9. Liposome formulations include 30:70 molar ratio of PS:PC, 15:15:70 molar ratio of PS:Lyso-PS:PC, and 30:70 molar ratio of Lyso-PS:PC. One group of animals received buffer as an immunization control. After a two week washout, all animals sacrificed and plasma collected for analysis.

Example 3

Figure 1:
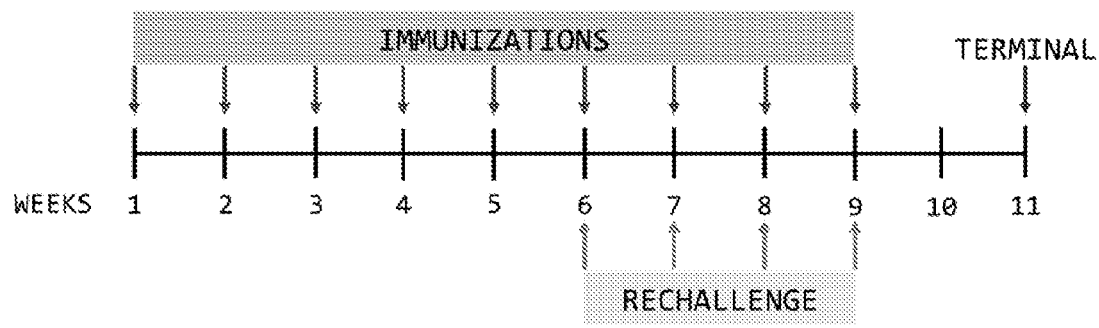

This example describes continuous tolerance induction to an antigen. Male and female knockout mice (n=7) were used per group. 0.4 µg of FVIII in TRis buffer (150 mM NaCl, 25 mM TRIS, pH 7.0), endotoxin-free was used. The protein to lipid ratio was 1:10,000. Immunizations were done by oral gavage or subcutaneous route. Rechallenge (meaning administration of a second composition) was done by iv route, 24 hours after immunizations. The various treatment groups were: free FVIII, PS FVIII, 15% lyso-PS FVIII (lyso-PS:PS:PC 15:15:70), 30% lyso-PS FVIII (lyso-PS:PC 30:70). The scheme is shown in FIG. 1.

Figure 2:
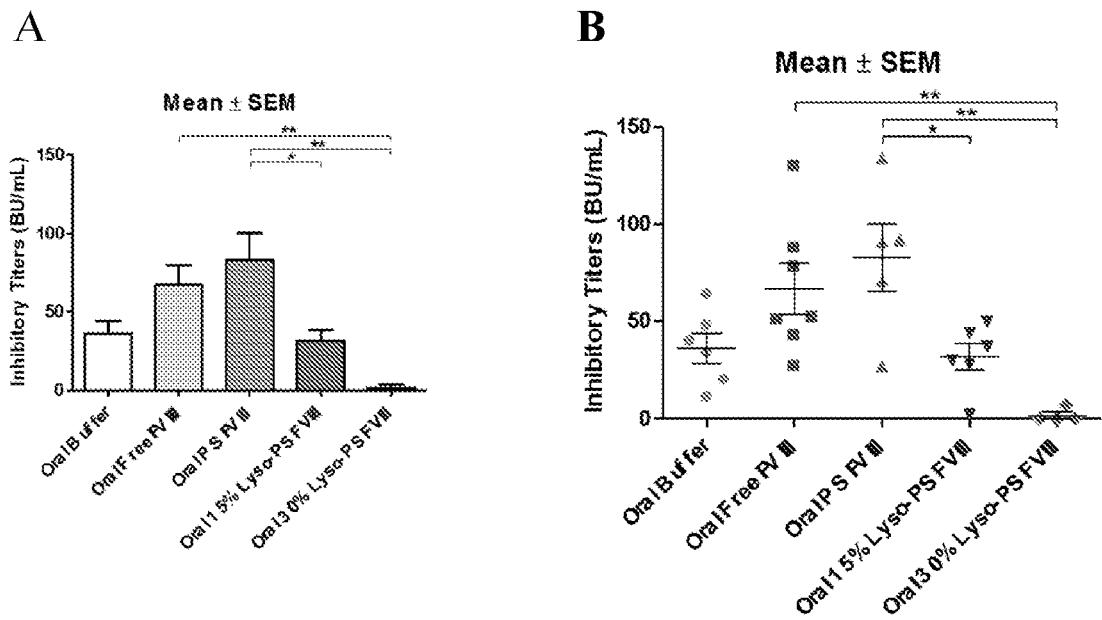
Figure 3:
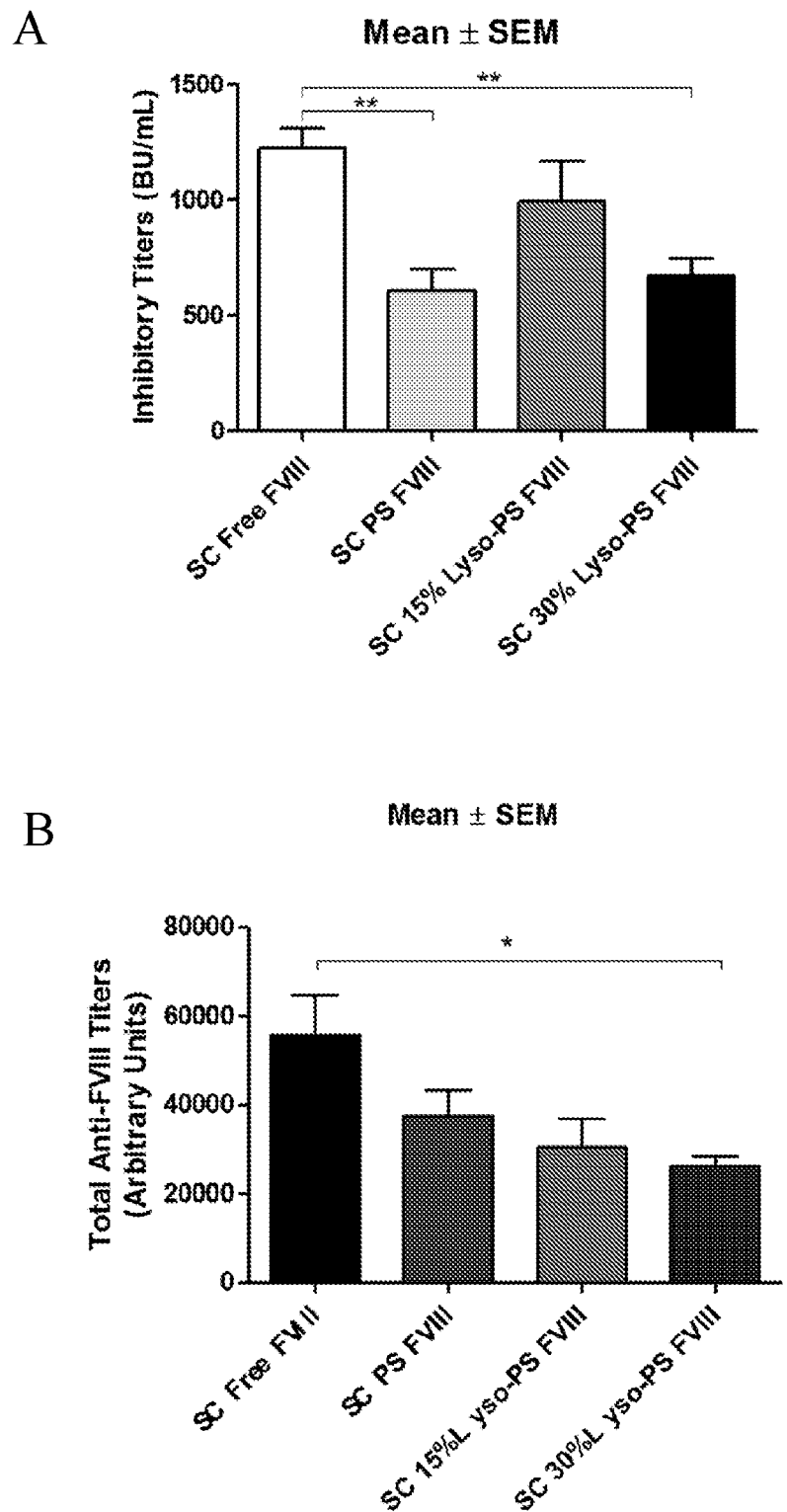

The results are shown in FIGS. 2 and 3. FIG. 2 shows oral administration of the first composition, while FIG. 3 shows subcutaneous administration of the first composition. As can be seen from the figures, while both PS and lyso-PS were able to induce tolerance when the compositions were administered via the subcutaneous route (FIG. 3), only lyso-PS was able to induce tolerance via the oral route (FIG. 2). Further, a 30% lyso-PS was more effective in inducing tolerance than 15%.

Figure 4:
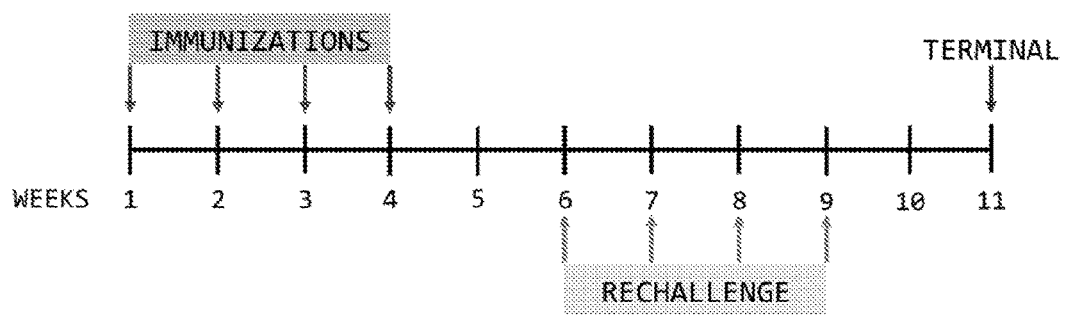
Figure 5:
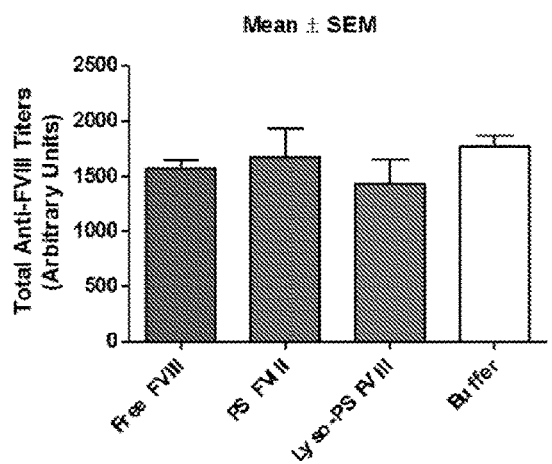
Figure 5:
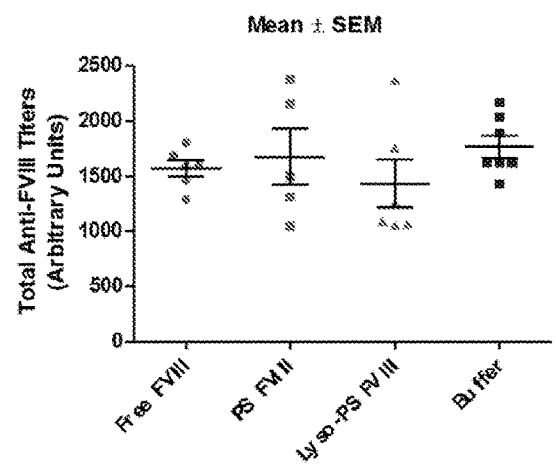

When the PS and the lyso-PS compositions were administered via an oral route for the first composition but not on a continuous basis and rechallenged via iv route, the advantage seen with lyso-PS with continuous administration was not observed. The scheme for this experiment is shown in FIG. 4 and the results are shown in FIG. 5. Comparing the results of FIG. 5 with the results of FIG. 2, it can be seen that to exploit the full advantage seen with lyso-PS, the priming compositions are preferably administered on a continuous basis while overlapping with the administration of the second composition.

Example 4

This example describes the reversal of established antibody titers upon administration of lyso-PS compositions.

Reversal Study.

Age-matched and gender-matched HA mice was used with n=14 per treatment group. Each animal received 0.4 µg FVIII in Tris buffer (150 mM NaCl, 25 mM Tris, pH 7.0) that was endotoxin free. A 1:10000 protein:lipid molar ratio was used. Animals received 0.4 µg of FVIII subcutaneously once a week for 4 weeks in order to induce titers. One week after the last injection, all animals received 0.4 µg of FVIII in the presence or absence of PS and Lyso-PS liposomes via oral immunization once a week for four weeks. One group of animals was immunized with buffer alone as a control. One group of animals (n=6) was sacrificed at week 5 to obtain baseline titers. One week after the last oral gavage, half the animals in each treatment (n=7) were sacrificed and plasma collected for analysis. All remaining animals receive 0.4 µg FVIII IV via the tail vein once a week for four weeks for the re-challenge. After a two week washout, all animals sacrificed; plasma collected for analysis of total anti-FVIII titers and neutralizing titers.

Figure 6:
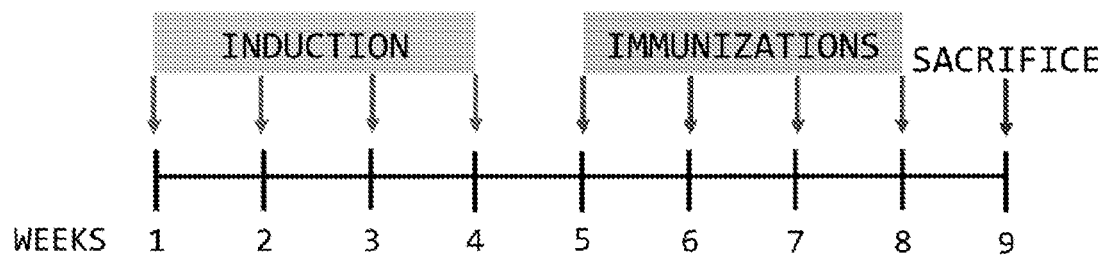
Figure 7:
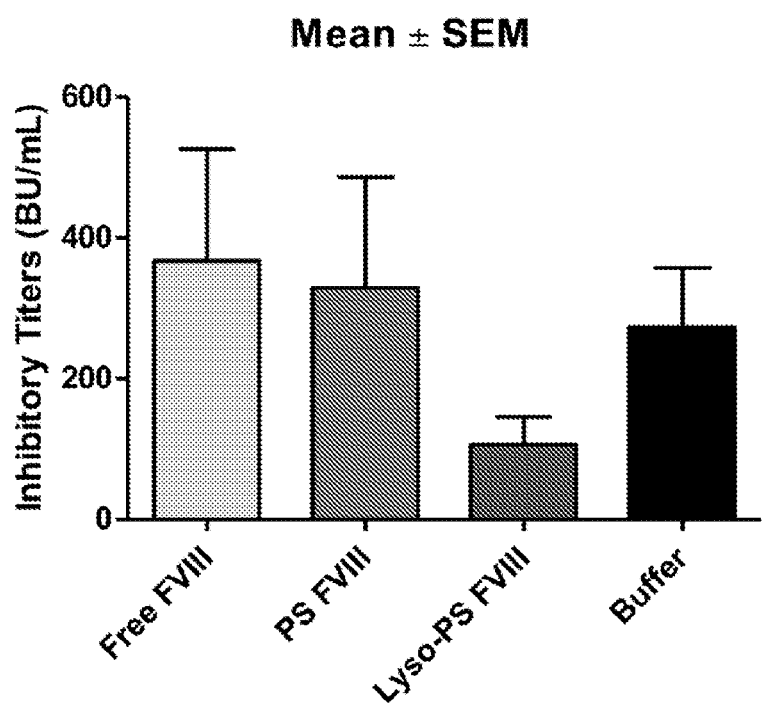

The scheme for this example is illustrated in FIG. 6 and the results are shown in FIG. 7. While PS liposomes were unable to result in any statistically significant reduction in established antibodies, lyso-PS liposomes were able to significantly reduce established antibody titer.

Example 5

This example describes specificity for the induction of immune tolerance.

Immunogenicity Study.

The relative immunogenicity of lyso-PS-FVIII and its ability to induce tolerance was evaluated in HA mice. HA mice (n=8/group) were pre-treated with sub-therapeutic dose of 1 µg antigen subcutaneous (SC) or oral in the presence and absence of PS once a week for four weeks. Two weeks after the last immunization, mice were re-challenged with 1 µg of free antigen SC or iv once a week for seven weeks. A blood sample was taken from to follow antibody development. Two weeks after the last re-challenge, all mice were sacrificed and plasma collected via cardiac puncture in 10% v/v acid citrate dextrose solution. Plasma samples were stored at −80° C. until further analysis.

FVIII Antigen Specificity Immunogenicity Study

Animal studies were conducted in GFP-FoxP3 HA mice. Mice (n=21/group) were immunized with four weekly SC injections of 0.4 µg of FVIII in the presence and absence of Lyso-PS. Two weeks after the last injection, 7 animals per group were sacrificed and plasma samples were collected as baseline samples for relative immunogenicity analysis of antibody titers. Half of the remaining animals in each treatment group were then re-challenged with two weekly SC injections of 0.4 µg of free FVIII while the other remaining animals were re-challenged with two weekly SC injections of 0.4 µg of Ovalbumin (Ova). Two weeks after the last re-challenge, all animals were sacrificed and plasma collected via cardiac puncture in 10% v/v acid citrate dextrose solution. Plasma samples were stored at −80° C. until further analysis.

Figure 8:
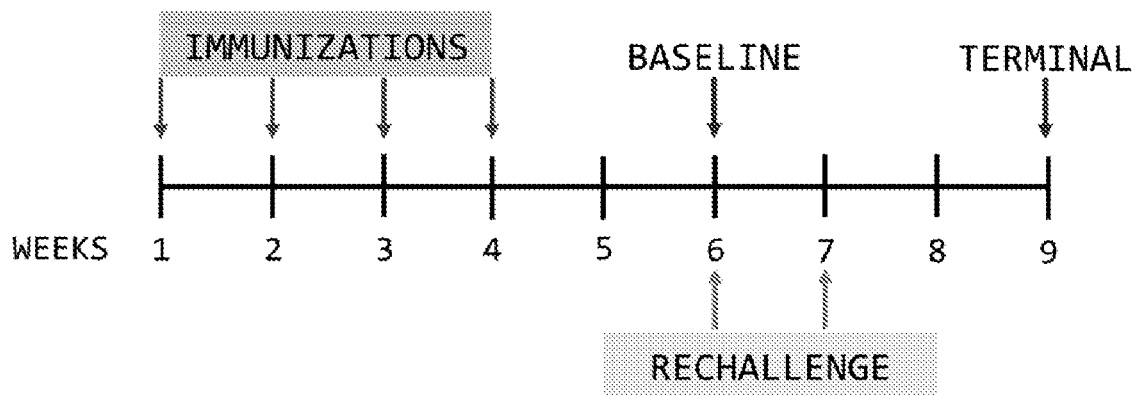
Figure 9:
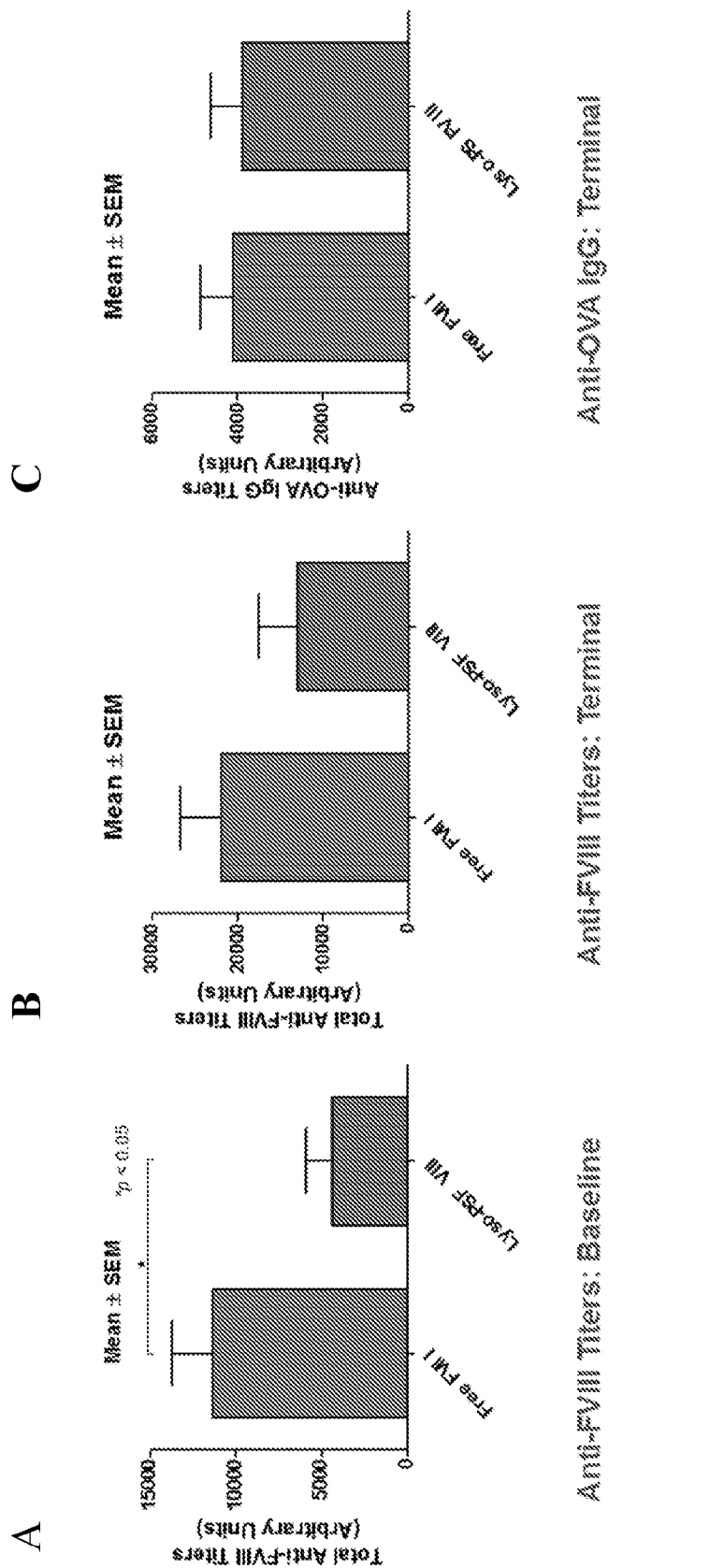
Figure 10:
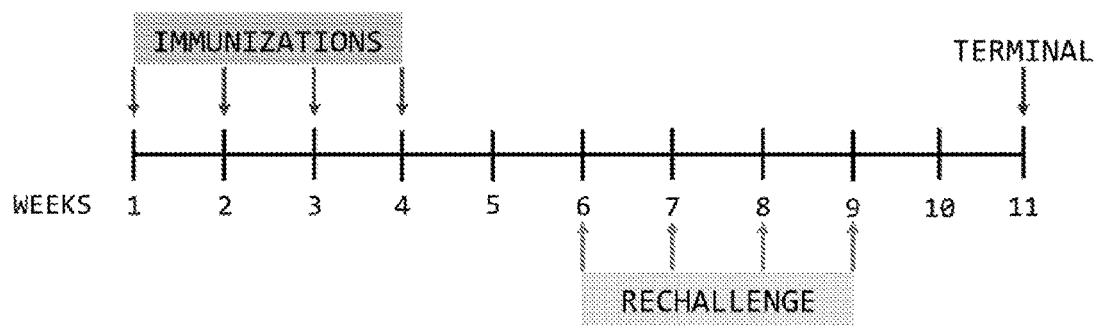
Figure 11:
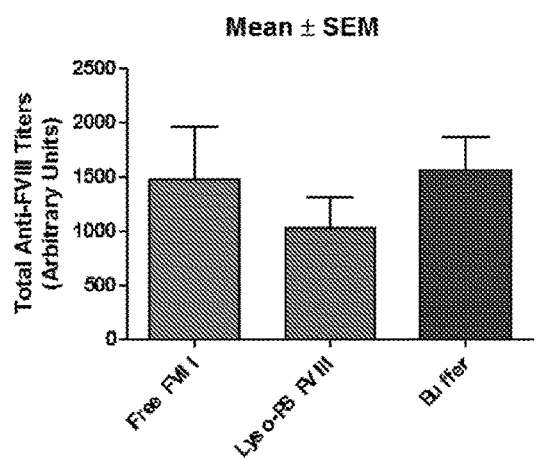
Figure 11:
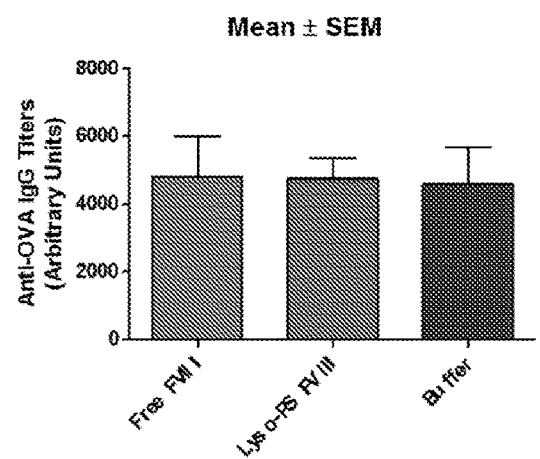

The schemes for these experiments is shown in FIGS. 8 and 10, and the results are shown in FIGS. 9 and 11. These results show that specificity for the immune tolerance for the protein is seen with lyso-PS for the subcutaneous route as well as the oral route.

Example 6

Role of TIM-4 Immunogenicity Study.

Animal studies were conducted in GFP-FoxP3 HA mice. Mice (n=12-14/group) were immunized with four weekly SC injections of 0.4 µg FVIII in the presence and absence of PS and lyso-PS. The group of mice that received PS and lyso-PS received SC immunization of 15 µg of a function-blocking anti-TIM-4 antibody. Thirty minutes after the administration of the anti-TIM-4 antibody, mice in these groups received a SC injection of PS-FVIII (0.4 µg) and lyso-PS Factor VIII in close proximity to the administered anti-TIM-4 antibody. Following a two week washout period, half the animals from each group were sacrificed and plasma samples were collected as baseline samples for relative immunogenicity analysis of antibody titers. All remaining animals were re-challenged with two weekly SC injections of 0.4 µg of free FVIII alone. Two weeks after the last re-challenge injection, all mice were sacrificed and plasma collected via cardiac puncture in 10% v/v acid citrate dextrose solution. Plasma samples were stored at −80° C. until further analysis. The animals that received PS or lyso PS exhibited lower antibody titers compared to animals that received free FVIII. However, administration of TIM-4 antibody reversed the effect of PS/Lyso mediated effects suggesting involvement of this receptor. Additional receptors and unique receptors for PS and Lyso are also possible.

Example 7

Figure 12:
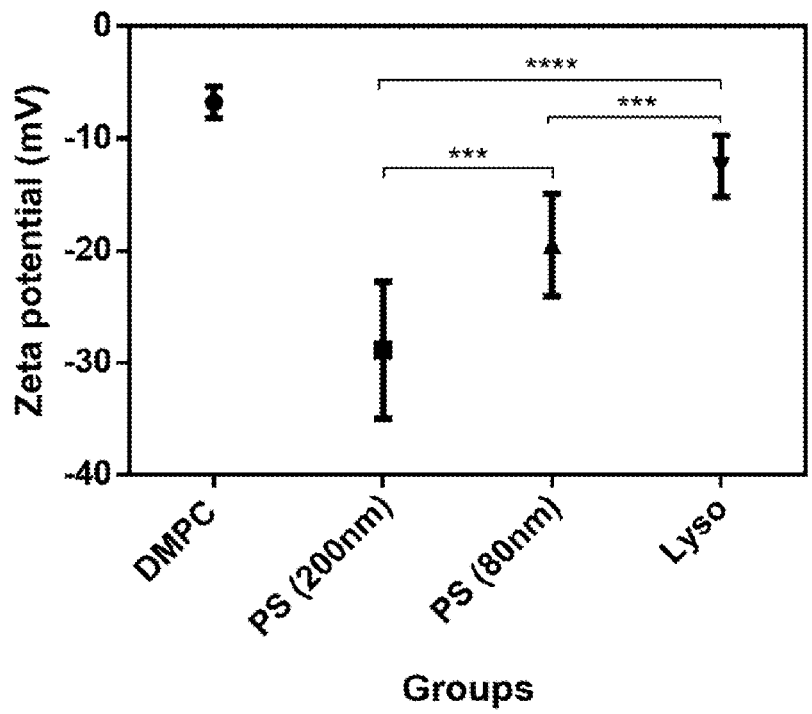
FIG. 12 shows the zeta potential of DMPC, PS (200 nm), PS (80 nm) and lyso-PS.
Figure 13:
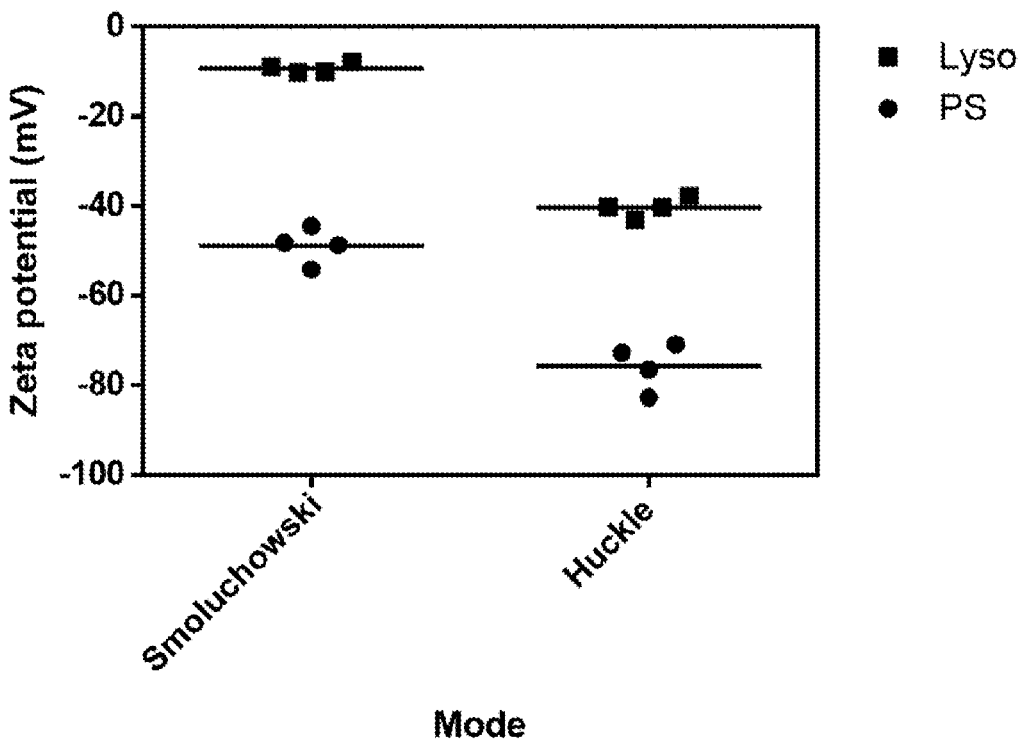
FIG. 13 shows the zeta potential of Lyso-PS and PS. The zeta potential was determined using the Smoluchowski mode and the Huckle mode.

This example describes the biophysical characteristics of Lyso-PS-containing liposomes compared to the conventional PS liposomes. Undesirable immune response against therapeutic proteins is one of the major clinical complications of protein based therapy. Different structures of PS acyl chain, such as chain length, degree of saturation, and number of chains, were investigated to determine contributions to the tolerogenic effect of PS. Lyso-PS liposomes were found to be much smaller in size compared to PS liposomes, despite the similar preparation procedure. Due to the small size, lyso PS liposomes were expected to have a larger surface charge density compared to PS liposomes. The surface charge of PS and Lyso PS liposomes were therefore investigated through the measurement of zeta potential. Even when extruded through a 200 nm filter membrane, lyso-PS liposomes had a much smaller mean particle size (106.9 nm) compared to DMPC and PS liposomes prepared with the same filter membrane (194.4 and 162.4 nm, respectively) (Table 2 and FIG. 12). In order to have a better characterization and comparison in term of surface charge between PS and Lyso PS liposomes with respect to size, the size of PS liposomes were matched with Lyso-PS using an 80 nm filter membrane. Mean particle size of this PS liposomes were reported to be 117.2 nm. PS liposome extruded through a 200 nm filter membrane was observed to have the highest magnitude of zeta potential, −28.9±3.0 mV. However, surprisingly, zeta potential of PS 80 nm liposome and Lyso PS 200 nm liposome were significantly lower (−19.5±4.6 mV and −12.4±2.7 mV, respectively). As zeta potential measures the electrostatic potential between charges of the diffuse layer rather than the actual surface charge of the particle, the presence of high salt concentration within the buffer solvent can possibly obscure the orientation of ions within the diffuse layer, thereby masking the true surface charge of the vesicles. An attempt to remove the solvent ions was conducted by replacing Tris buffer with deionized water. Nevertheless, zeta potential of Lyso PS liposome was still observed to be lower than that of size-matched PS liposome (−40.3±2.2 mV vs. −75.7±5.2 mV) (FIG. 13). This suggests that the reduction in particle size may not directly lead to a higher surface charge, and the tolerogenic effect of Lyso PS may not be due to the elevated surface charge of the vesicle.

TABLE 2

| Samples | Filter membrane size (nm) | Mean particle size (nm) | SD |
| --- | --- | --- | --- |
| DMPC (100%) | 200 | 194.4 | 26.59 |
| 30% PS (PC:PS 70:30) PS from brain (mostly 18:1 and 18:0) | 200 | 162.4 | 4.383 |
| 30% PS (PC:PS 70:30) PS from brain (mostly 18:1 and 18:0) | 80 | 117.2 | 18.80 |
| 30% lyso (PC:lyso-PS 70:30) (lyso PS is single chain 18:1) | 200 | 106.9 | 6.945 |
| 30% 18:1 (PC:PS 70:30), PS is purified 18:1, double chain | 200 | 202 | 7.1 |
| 30% lyso (PC:lyso PS 70:30) (lyso PS is single chain 16:0) | 200 | 213.8 | 4.02 |

Example 8

This example describes Lyso PS containing particles. In addition to size and zeta potential, the stability as well as phase properties of Lyso-PS liposome and other novel tolerogenic lipid particles containing Lyso-PS were investigated using differential scanning calorimetry (DSC) and temperature-dependent fluorescence anisotropy measurements. For the DMPC-Lyso PS liposome, four groups of liposome containing DMPC and Lyso PS with the mole percent composition of DMPC:Lyso PS as 100:0, 90:10, 80:20, and 70:30 were prepared using the dry film method. These lipid films were then rehydrated in PBS at the temperature of 37° C. Since DMPC was the base lipid, the group with the composition of 100:0 was used as the positive control. The total lipid concentration of all groups was maintained at 40 mM. For DSC measurement, 15 uL of each liposome preparation were then packed into an Aluminum pan and sealed with a cover using a crimper. A reference pan was used with an equal amount of water. Samples were scanned from 5 to 40° C. at a heating rate of 5° C./min under $N_2$ flow of 20 ml/min, and samples' equilibration time was set to 3 minutes at 5° C. prior to each scanning.

Figure 14:
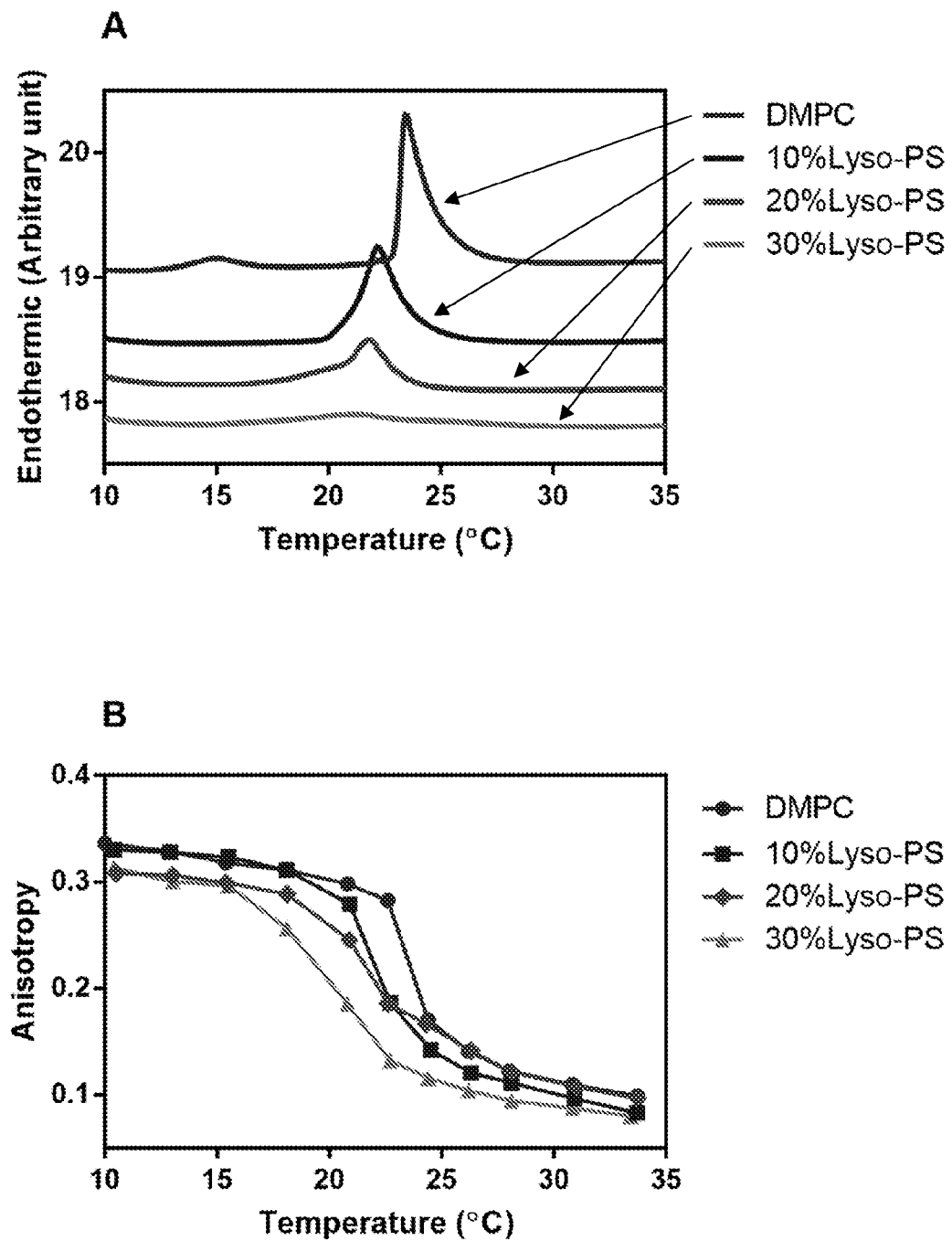
FIG. 14 shows A) a differential scanning calorimetry (DSC) thermogram of DMPC, 10% Lyso-PS, 20% Lyso-PS, and 30% Lyso-PS. B) Temperature-dependent fluorescence anisotropy of DMPC, 10% Lyso-PS, 20% lyso-PS, and 30% lyso-PS.

For visual observation, as the mole percent of lyso Ps in the liposome increased, the turbidity of the sample decreased. This might be due to the reduction of vesicle size as the phospholipids self-resembled into the bilayer structure. As shown in FIG. 14A, the control DMPC liposome showed a main transition spike at 23° C. and a broad pre-transition peak at 15° C. As the mole percent of lyso PS in the composition increased, the peak area decreased and the pre-transition phase also disappeared. In addition, the peak was shifted to a lower temperature. At the composition of 70:30, only a small bump was observed from the DSC curve. This suggests that DMPC and lyso PS are miscible at this 70:30 mole percent and phase separation is very minimal.

This observation was further confirmed by fluorescence polarization studies. The liposomal composition was labeled with diphenylhexatriene DPH and fluorescence polarization was measured as a function of temperature. For DMPC the polarization/anisotropy was at higher at lower temperatures such as 15° C. when the formulation exists in gel phase but decreases as it undergoes transition (FIG. 14B). The midpoint of transition is centered around 23° C. similar to that observed with DSC. But the addition of lyso-PS showed a shift in transition to lower temperatures similar to that observed in DSC studies. These observations show that DMPC and lyso PS are stable where the two components are miscible.

Example 9

Figure 15:
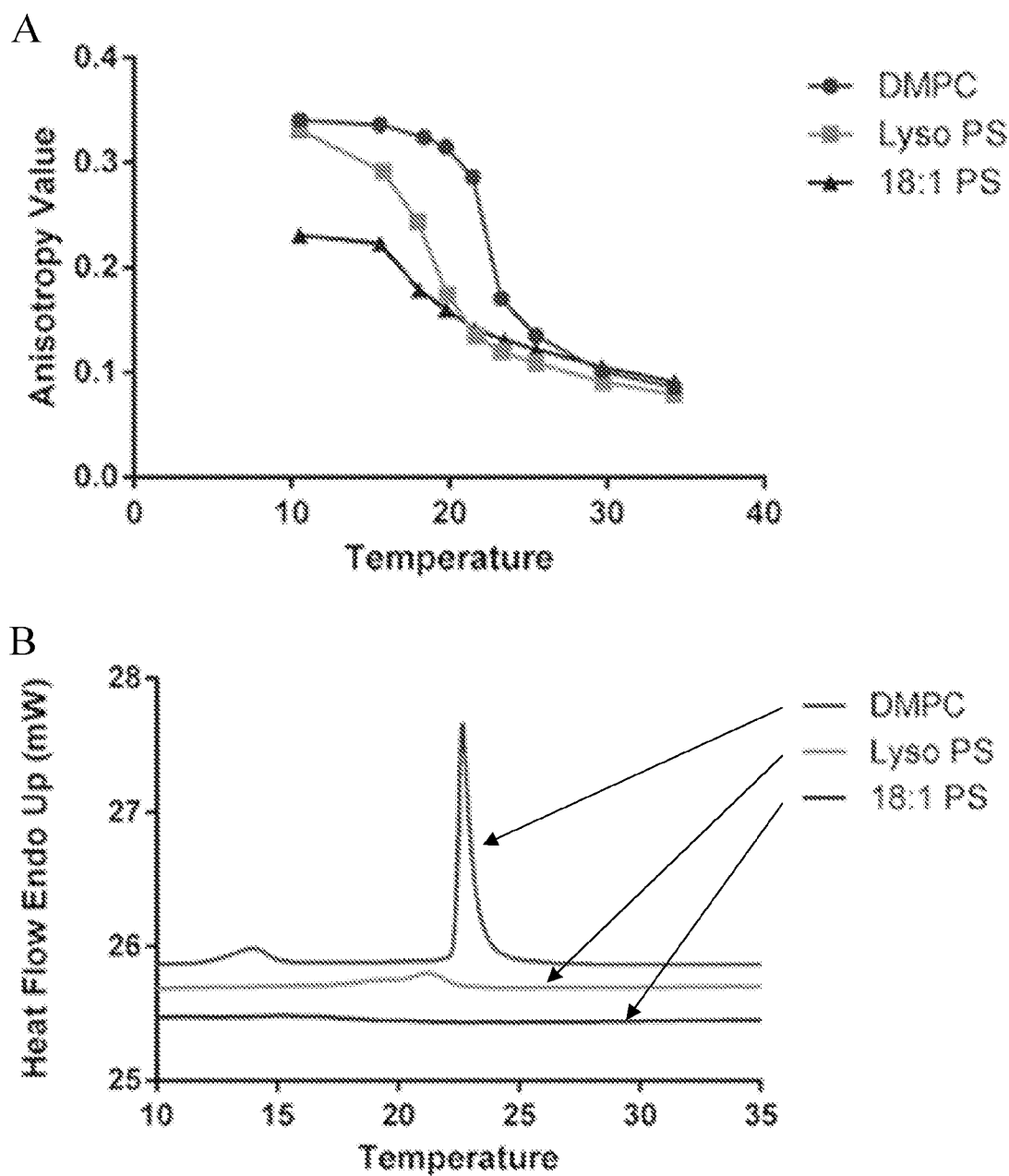
FIG. 15 shows A) temperature-dependent fluorescence anisotropy of DMPC, lyso-PS, and 18:1 PS. B) A DSC thermogram of DMPC, lyso-PS, and 18:1 PS.

This example provides a comparison between double chain and single chain PS containing liposomes. Anisotropy and DSC measurements were obtained as described in Example 8 above. Results are shown in FIGS. 15A and 15B. As is clear based on DSC studies, size and zeta potential analysis and anisotropy studies, 18:1 double chain effect is more pronounced in terms of phase properties from 18:1 but lyso induces curvature likely leading to small size.

Example 10

This example describes DMPC-lyso PS-Retinoic acid or rapamycin containing liposomes. The phase properties of liposome containing DMPC-lyso PS-Retinoic acid (RA) or rapamycin were investigated using DSC.

Method:

For the DMPC-Lyso PS-Retinoic acid liposome four groups of liposome containing DMPC, Lyso PS, and RA with the mole percent composition of DMPC:Lyso PS:RA as 70:30:0, 70:29:1, 70:27:3, and 70:25:5 were prepared. In addition, a liposome sample containing only DMPC and RA with the mole percent composition of 95:5 was also made to further investigate the phase properties as well as the intercalation of RA into the bilayer structure of DMPC. All samples were prepared using the dry film method and these lipid films were then rehydrated in PBS at the temperature of 37° C. DMPC was used as the base lipid and the DMPC:Lyso PS:RA group with the composition of 70:30:0 was used as the positive control. The total lipid concentration of all groups was maintained at 40 mM. An old sample of DMPC 40 mM from the previous DSC study on DMPC: Lyso PS was also included for reference and comparison purposes. For DSC measurement, 15 µL of each liposome preparation were packed into an Aluminum pan and sealed with a cover using a crimper. A reference pan was used with an equal amount of water. Similar to the previous DSC study on DMPC and Lyso PS, as the base lipid was DMPC, samples were scanned from 5 to 40° C. at a heating rate of 5° C./min under $N_2$ flow of 20 ml/min. Equilibration time for samples was set to 3 minutes at 5° C. prior to each scanning.

DSC thermogram for liposomes comprising both Lyso-PS and RA shows that the main transition peak of pure DMPC vesicles occurred at around 23° C., as the lipid lamellar structure underwent gel to liquid crystalline phase transition. The inclusion of 10, 20, and 30 mol % of Lyso-PS into the bilayer resulted in the broadening and shift of DMPC transition peak to a lower temperature. This suggests that Lyso-PS partitioned into the bilayer and induced changes in the DMPC lamellar properties. In the presence of 30 mol % of lyso-PS, the peak was almost completely abolished, indicating the cooperation of the mixed system as no phase separation occurred. This further indicates that the stability of DMPC:Lyso-PS vesicle was ideal at 70:30 molar ratio. Consistent with the data obtained from DSC, anisotropy values of DPH-labeled liposomes also showed that the addition of increasing concentration of Lyso-PS into the DMPC bilayer introduced a shift and slight broadening of the transition phase to a lower temperature. This suggests that Lyso-PS partitioned into the DMPC bilayer and induced the fluid phase formation of the vesicle at a lower temperature (FIG. 16A). Similar to the addition of Lyso-PS into DMPC bilayer, the addition of RA alone also resulted in the broadening and shift of DMPC melting profile to a lower temperature on DSC thermogram and anisotropy-value curve. This indicates that RA partitioned into the acyl chain region and induced the formation of fluid phase when introduced into the DMPC bilayer (FIG. 16A). Although the inclusion of either Lyso-PS or RA produced a broadening and shift of DMPC phase transition to a lower temperature, the mixing of Lyso-PS and RA at 70:30:5 molar ratio (DMPC:Lyso-PS:RA) together completely abolished the DMPC phase transition on both DSC thermogram (FIG. 16A) and anisotropy-value curve (FIG. 16B). This illustrates that both components partitioned into the DMPC bilayer, synergistically induced changes but no phase separation occurred. The reduction of fluorescence anisotropy intensity in the presence of PS, Lyso-PS, and RA compared to the control DMPC liposome also represented the free rotation of the DPH probe as the motion of the acyl chain increased and the chain packing decreased. This is a characteristic of the packing defect of the vesicles, which can allow more space for an efficient loading of a protein or penetration of water for protein-solvent interaction. As a result, the mixing of Lyso-PS and RA into the DMPC bilayer creates a stable lipid particle which can potentiate a better loading efficiency and delivery of protein therapeutics with lower immunogenicity. Similar observations were made for Rapamycin loaded in Lyso PS containing particles (FIG. 16C).

Example 11

This example demonstrates that lyso-PS liposomes can be complexed to a variety of proteins. For example, complexes of lyso-PS liposomes were prepared with alpha glucosidase (GAA), collagen, gliadin, MOG peptides, Ova and collagen. The preparation of lipid particles involved loading and separation of liposomes loaded with antigens from free antigens using sephadex column and antigen associated with LysoPS was estimated using protein quantitation analysis and the fluorescence spectroscopy analysis. Association efficiency for GAA was observed to be 44%, for gliadin to be 90% and for collagen to be 62%. An example of separation and fluorescence spectrum is shown for collagen.

Liposomes were prepared in a 30:69:1 ratio of LysoPS: PC:rhodamine PE. The preparation was then placed into the rotary evaporator to form the lipid film, then rehydrated with TRIS buffer, and extruded (×6) to achieve final size of approximately 100 nm. The amount of liposomes was confirmed by phosphate assay.

The size exclusion column was prepared the day before the column run by hydrating one gram of G-200 sephadex beads in 35-40 mL of TRIS buffer; the preparation was then shaken until gel formed, then loaded into the column. 2.5 µl of collagen and 497.5 µl TRIS buffer were used to prepare 500 µl of free collagen sample. 2.5 µl of collagen, 401.2 µl TRIS buffer, and 96.3 µl lysoPS preparation were used to prepare 500 µl of the lyso-Collagen sample.

Free-collagen sample was run through the column; thirty fractions were collected. After washing the column with TRIS buffer, one hundred microliters of 30% lyso-collagen sample was run through the column and thirty fractions were collected. The thirty lyso-collagen fractions were then read by fluorescence spectrophotometry (emission wavelength=580 nm, excitation=560 nm). BCA assay was used to quantify protein amount in Lyso-collagen sample and in free-collagen sample. (FIG. 17). Association calculations were as follows. The protein:lipid ratio used is 1:10,000. The molecular weight of collagen is 300,000 g/mol. The collagen dose used for this experiment is 5 µg. The concentration of the collagen aliquot used for this experiment is 2 µg/µL. The actual concentration of the LysoPS preparation (confirmed by phosphate assay) was 1.731 µmol/µL.

Example 12

This example describes fluorescence for lyso-PS liposomes complexed with gliadin. Gliadin fluorescence and its first derivative spectra: As shown in FIGS. 18A and 18B, gliadin loaded in lyso PS shows about 7 nm shift in emission maxima suggesting that gliadin is intercalated in the bilayer.

The preceding description provides specific examples of the present invention. Those skilled in the art will recognize that routine modifications to these embodiments can be made which are intended to be within the scope of the invention.

What is claimed is:
1. A composition comprising a plurality of liposomes, wherein the liposomes comprise phosphatidylcholine (PC) and lysophosphatidylserine (lyso-PS), wherein the ratio of PC to lyso-PS is from 90:10 to 60:40, and wherein the acyl chain of the lyso-PS is oleic acid.

2. The composition of claim 1, wherein the ratio of PC to lyso-PS is from 85:15 to 70:30.

3. The composition of claim 1, wherein the PC is present as dimyristoyl-sn-glycero-3 phosphatidylcholine (DMPC).

4. The composition of claim 1, wherein the size of the liposomes is from 80 to 150 nm.

5. The composition of claim 1, wherein the zeta potential of the liposomes is from −10 to −15.

6. The composition of claim 1, wherein the liposomes are complexed to an antigenic polypeptide.

7. The composition of claim 1, wherein PC and lyso-PS are the only phospholipids present in the bilayer of the liposome.

8. The composition of claim 1 further comprising retinoic acid wherein the ratio of PC, PS and retinoic acid is 70:20:10 to 70:29:1.

9. The composition of claim 1 further comprising rapamycin wherein the ratio of PC, PS and rapamycin is 70:20:10 to 70:29:1.

10. The composition of claim 1, wherein 99% of the liposomes have a diameter of less than 250 nm and 90% have a diameter of less than 160 nm.

11. The composition of claim 10, wherein 90% of the liposomes have a diameter of from 50 to 150 nm.

12. The composition of claim 1, wherein the liposomes are complexed to a therapeutic protein, a diagnostic protein, a self-antigen, a neo-antigen, an allergen.

13. The composition of claim 12, wherein the target protein is FVIII, insulin, acid alpha glucosidase (GAA), myelin oligodendrocyte glycoprotein (MOG) peptide (35-55), ovalbumin (OVA), gliadin, collagen, adeno associated virus (AAV) capsid protein.

14. The composition of claim 1, wherein 90% of the liposomes have a diameter of from 50 to 150 nm and a zeta potential of from −10 to −17.

15. The composition of claim 12, wherein the protein lipid molar ratio is 1:1,000 to 1:5,000.

* * * * *

UNITED STATES PATENT AND TRADEMARK OFFICE
CERTIFICATE OF CORRECTION

PATENT NO. : 11,083,782 B2
APPLICATION NO. : 16/091425
DATED : August 10, 2021
INVENTOR(S) : Balu-Iyer et al.

Page 1 of 1

It is certified that error appears in the above-identified patent and that said Letters Patent is hereby corrected as shown below:

In the Specification

Column 1, Lines 12-17 should read:
--STATEMENT REGARDING FEDERALLY SPONSORED RESEARCH OR DEVELOPMENT
This invention was made with government support under contract no. HL070227 awarded by the National Institutes of Health. The government has certain rights in the invention.--

Signed and Sealed this
Third Day of June, 2025

Coke Morgan Stewart
*Acting Director of the United States Patent and Trademark Office*